United States Patent
Matsumoto et al.

(10) Patent No.: US 9,872,907 B2
(45) Date of Patent: Jan. 23, 2018

(54) HYDROGEL-FORMING MATERIAL, PREMIX, AND HYDROGEL FORMATION METHOD

(71) Applicant: NISSAN CHEMICAL INDUSTRIES, LTD., Tokyo (JP)

(72) Inventors: Keigo Matsumoto, Funabashi (JP); Tsubasa Kashino, Funabashi (JP)

(73) Assignee: NISSAN CHEMICAL INDUSTRIES, LTD., Tokyo (JP)

(*) Notice: Subject to any disclaimer, the term of this patent is extended or adjusted under 35 U.S.C. 154(b) by 2 days.

(21) Appl. No.: 14/433,529

(22) PCT Filed: Oct. 2, 2013

(86) PCT No.: PCT/JP2013/076843
§ 371 (c)(1),
(2) Date: Apr. 3, 2015

(87) PCT Pub. No.: WO2014/054702
PCT Pub. Date: Apr. 10, 2014

(65) Prior Publication Data
US 2015/0250880 A1    Sep. 10, 2015

(30) Foreign Application Priority Data
Oct. 3, 2012 (JP) ................. 2012-221652

(51) Int. Cl.
| | | |
|---|---|---|
| A61K 47/18 | (2017.01) | |
| A61K 8/64 | (2006.01) | |
| A61K 9/06 | (2006.01) | |
| A61K 8/36 | (2006.01) | |
| A61K 8/37 | (2006.01) | |
| A61Q 19/00 | (2006.01) | |
| A61K 8/81 | (2006.01) | |
| A61K 8/04 | (2006.01) | |
| A61L 15/34 | (2006.01) | |
| A61K 47/12 | (2006.01) | |
| A61K 47/32 | (2006.01) | |
| C08K 5/098 | (2006.01) | |
| C08K 5/20 | (2006.01) | |

(52) U.S. Cl.
CPC .......... *A61K 47/183* (2013.01); *A61K 8/042* (2013.01); *A61K 8/361* (2013.01); *A61K 8/37* (2013.01); *A61K 8/64* (2013.01); *A61K 8/8147* (2013.01); *A61K 8/8152* (2013.01); *A61K 9/06* (2013.01); *A61K 47/12* (2013.01); *A61K 47/32* (2013.01); *A61L 15/34* (2013.01); *A61Q 19/00* (2013.01); *C08K 5/098* (2013.01); *C08K 5/20* (2013.01); *A61K 2800/10* (2013.01)

(58) Field of Classification Search
CPC ...... A61K 47/183; A61K 47/32; A61K 47/12; C08K 5/20; C08K 5/098
See application file for complete search history.

(56) References Cited

U.S. PATENT DOCUMENTS

| | | |
|---|---|---|
| 2012/0035108 A1 | 2/2012 | Miyamoto et al. |
| 2012/0258059 A1 | 10/2012 | Iwama et al. |
| 2013/0084305 A1 | 4/2013 | Iwama et al. |
| 2015/0202586 A1 | 7/2015 | Imoto et al. |

FOREIGN PATENT DOCUMENTS

| | | |
|---|---|---|
| EP | 2865442 A1 | 4/2015 |
| JP | H08-53693 A | 2/1996 |
| WO | 2009/005151 A1 | 1/2009 |
| WO | 2009/005152 A1 | 1/2009 |
| WO | 2010/106981 A1 | 9/2010 |
| WO | 2011/052613 A1 | 5/2011 |
| WO | 2012/063947 A1 | 5/2012 |
| WO | 2012/133787 A1 | 10/2012 |
| WO | 2012/144609 A1 | 10/2012 |

OTHER PUBLICATIONS

Suzuki et al., "Supramolecular Hydrogels Formed by L-Lysine Derivatives," Chemistry Letters, 2004, vol. 33, No. 11, pp. 1496-1497.
Jung et al., "Self-Assembly of a Sugar-Based Gelator in Water: Its Remarkable Diversity in Gelation Ability and Aggregate Structure," Langmuir, vol. 17, 2001, pp. 7229-7232.

(Continued)

*Primary Examiner* — Wenwen Cai
(74) *Attorney, Agent, or Firm* — Oliff PLC

(57) ABSTRACT

A hydrogel-forming material, a premix, and a method for forming a hydrogel through a simple process at room temperature. The material including: a disperse phase (A) including a lipid peptide-based gelator including at least one of a compound of Formula (1) or pharmaceutically usable salt thereof, water, and a fatty acid salt; and a phase (B) that includes a water-soluble acidic polymer:

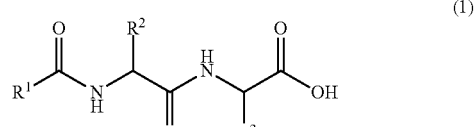

(1)

(where $R^1$ is a $C_{9\text{-}23}$ aliphatic group, $R^2$ is a hydrogen atom or a $C_{1\text{-}4}$ alkyl group that optionally has a $C_{1\text{-}2}$ branched chain, $R^3$ is a —$(CH_2)_n$—X group, n is a number of 1 to 4, X is an amino group, a guanidino group, a —$CONH_2$ group, a 5-membered ring optionally containing 1 to 3 nitrogen atom(s), a 6-membered ring optionally containing 1 to 3 nitrogen atom(s), or a condensed heterocycle that contains a 5-membered ring and a 6-membered ring optionally containing 1 to 3 nitrogen atom(s)).

10 Claims, No Drawings

(56) References Cited

OTHER PUBLICATIONS

Hamachi et al., "Solid-Phase Lipid Synthesis (SPLS)-2: Incidental Discovery of Organogelators Based on Artificial Glycolipids," Tetrahedron Letters, 2001, vol. 42, pp. 6141-6145.

Hamachi et al., "Solid Phase Lipid Synthesis (SPLS) for Construction of an Artificial Glycolipid Library," Chem. Commun., 2000, pp. 1281-1282.

Suzuki et al., "Supramolecular Hydrogel Formed by Glucoheptonamide of L-Lysine: Simple Preparation and Excellent Hydrogelation Ability," Tetrahedron, 2007, vol. 63, pp. 7302-7308.

Matsuzawa et al., "Assembly and Photoinduced Organization of Mono- and Oligopeptide Molecules Containing an Azobenzene Moiety," Adv. Funct. Mater., 2007, vol. 17, No. 9, pp. 1507-1514.

Jan. 7, 2014 International Search Report issued in International Application No. PCT/JP2013/076843.

Jan. 7, 2014 Written Opinion issued in International Application No. PCT/JP2013/076843.

Mar. 7, 2016 Extended Search Report issued in European Application No. 13843779.3.

HYDROGEL-FORMING MATERIAL, PREMIX, AND HYDROGEL FORMATION METHOD

TECHNICAL FIELD

The present invention relates to a hydrogel-forming material, a premix including a low-molecular lipid peptide-based gelator useful as a gelator, and a method for forming a hydrogel.

BACKGROUND ART

A hydrogel contains water as its medium and is therefore useful as a highly biocompatible gel. This gives a hydrogel a wide range of applications, for example, in the fields including daily necessities such as disposable diapers, cosmetics, and fragrances.

A conventional hydrogel is a polymer gel that is obtained from polymer chains crosslinked to form a three-dimensional network structure which is then bonded to a medium such as water through non-covalent bonds to cause swelling. The physical properties and the applications of such a polymer gel have been researched in large number on natural polymer gels containing a polysaccharide such as agarose and a protein and on synthetic polymer gels such as a acrylamide gel obtained by forming crosslinks between polymer chains through chemical covalent bonds.

Besides these gels that contain polymer compounds, a hydrogel that is obtained by self-assembling of an organic compound having relatively low molecular weight has been developed and extensively studied in recent years.

Most of the low-molecular gelators that have already been developed are amphiphilic compounds having a combination of a hydrophobic moiety that is a long-chain alkyl group and a hydrophilic moiety, and examples of these gelators include one having an amino acid [Non-patent Document 1], one having a peptide [Patent Documents 1 and 2], one having a saccharide [Non-patent Documents 2 and 3], and one having a polyol [Non-patent Document 4], as the hydrophilic moiety. In addition, a low-molecular gelator that utilizes the characteristics of a peptide consisting of valine to readily form a β-sheet structure has been developed [Non-patent Document 5].

Using the low-molecular hydrogelators described above, a hydrogel can be formed by stirring the hydrogelators and water as a medium with heating at the temperature of about 100° C. so that the hydrogelators are dissolved and dispersed in water, and by leaving the resulting solution still standing at room temperature.

PRIOR ART DOCUMENTS

Patent Documents

Patent Document 1: WO 2009/005151 pamphlet
Patent Document 2: WO 2009/005152 pamphlet

Non-Patent Documents

Non-patent Document 1: Suzuki, Masahiro. Yumoto, Mariko. Mutsumi, Shirai. Hirofusa, Hanabusa, Kenji. Chemistry Letters, 33(11), 1496-1497.
Non-patent Document 2: Jong Hwa Jung, Georeg John, Mitsutosish Mausda, Kaname Yoshida, Seiji Shinnkai, and Toshimi Shimizu Langumir 2001, 17, 7229-7232.
Non-patent Document 3: I. Hamachi, S. Kiyonaka, S. Shinkai, Tetrahedron Lett., 2001, 42, 6141.
I. Hamachi, S. Kiyonaka, S. Shinaki, Chem. Commun., 2000, 1281.
Non-patent Document 4: Masahiro Suzuki, Sanae Owa, Hirofusa Shirai and Kenji Hanabusa, Tetrahedron 2007 63 7302-7308.
Non-patent Document 5: Yoko Matsuzawa, Katsuyuki Ueki, Masaru Yoshida, Nobuyuki Tamaoki, Tohru Nakamura, Hideki Sakai, and Masahiko Abe, Adv. Funct. Mater. 2007, 17, 1507-1514.

SUMMARY OF THE INVENTION

Problem to be Solved by the Invention

Conventional methods disclosed at least by the present applicant for forming a gel with such low-molecular gelators are processes of heating and stirring so that the gelator is dissolved and dispersed in a medium and then leaving the system still standing at near room temperature for cooling, in other words, a single system process for gel formation.

However, with this single-system process, various problems have arisen as scaling up the hydrogel production.

One of the problems is that dissolving and dispersing the gelator in water serving as a medium need to be performed under conditions in which the temperature is as high as 100° C., which tends to cause denaturation of added ingredients. Therefore, additives that are easily affected by heat cannot be added, which in turn limits the applications of the resulting gel. Another problem is that conditions with high temperatures require more time for cooling to reach room temperature, which is disadvantageous in terms of productivity. Yet another problem is that high temperatures during production bring up safety issues and also increase production cost.

An additional problem is that, in the process of leaving the system in which a hydrogel is formed still standing at near room temperature after the gelator is dissolved and dispersed in water, the system is not uniformly cooled, causing the quality of the resulting hydrogel to be inconsistent. This is disadvantageous in terms of quality control.

As described above, the production conditions in the conventional single-system gel formation method are disadvantageous for hydrogel production on an industrial scale in terms of, for example, operability, cost, and quality control and performance of the resulting gel. In other words, further improvement has been demanded in large-scale hydrogel production in terms of productivity, production safety, and consistency in quality.

The present invention is devised based on the above circumstances, and an object of the present invention is to provide a hydrogel-forming material, a premix, and a method for forming a hydrogel, which can form a hydrogel through a relatively simple process and under relatively gentle conditions in terms of temperature (at room temperature).

Means for Solving the Problem

The inventors of the present invention have conducted intensive research to achieve the object and, as a result, have found that mixing a disperse phase including a gelator and a fatty acid salt with an acidic solution (disperse phase) results in an increase in viscosity to allow a hydrogel to be formed at room temperature and that the disperse phase including a gelator and a fatty acid salt can be kept in a liquid state at room temperature so as to be effectively used as a premix for hydrogel preparation.

More specifically, the inventors of the present invention have found that a gel can be prepared by stirring, at room temperature, a binary-system hydrogel-forming material that includes a disperse phase including a lipid peptide-based gelator consisting of a low-molecular lipid peptide or a pharmaceutically usable salt thereof, water, and a fatty acid salt, and a disperse phase including a water-soluble acidic polymer. Thus, the present invention has been completed.

The inventors of the present invention have also found that the lipid peptide-based gelator to which a fatty acid salt is added exhibits excellent dispersibility and solubility in water under gentler conditions than conventional conditions in terms of temperature, and such gelator can be suitably used as a gel premix material that can be stored at room temperature by being left to cool with stirring after heating.

Thus, the present invention relates to, as a first aspect, a hydrogel-forming material comprising: a disperse phase (A) including a lipid peptide-based gelator consisting of at least one of a compound of Formula (1) or a pharmaceutically usable salt thereof, water, and a fatty acid salt; and a disperse phase (B) that includes a water-soluble acidic polymer increasing viscosity by neutralization:

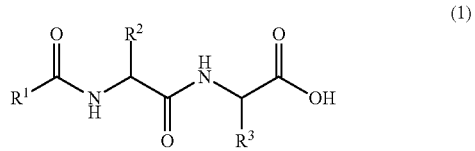
(1)

(where $R^1$ is a $C_{9-23}$ aliphatic group, $R^2$ is a hydrogen atom or a $C_{1-4}$ alkyl group that optionally has a $C_{1-2}$ branched chain, $R^3$ is a —$(CH_2)_n$—X group, n is a number of 1 to 4, X is an amino group, a guanidino group, a —$CONH_2$ group, a 5-membered ring optionally containing 1 to 3 nitrogen atom(s), a 6-membered ring optionally containing 1 to 3 nitrogen atom(s), or a condensed heterocycle that contains a 5-membered ring and a 6-membered ring optionally containing 1 to 3 nitrogen atom(s)).

As a second aspect, in the hydrogel-forming material according to the first aspect, the disperse phase (A) includes at least one fatty acid salt selected from the group consisting of butyrates, valerates, caproates, enanthates, caprylates, pelargonates, caprates, laurates, myristates, pentadecylates, palmitates, palmitoleates, margarates, stearates, oleates, vaccenates, linoleates, (9,12,15)-linolenates, (6,9,12)-linolenates, eleostearates, tuberculostearates, arachidates, arachidonates, behenates, lignocerates, nervonates, cerotates, montanates, and melissates.

As a third aspect, in the hydrogel-forming material according to the first aspect or the second aspect, the disperse phase including an acidic polymer is a disperse phase including polyacrylic acid or a carboxyvinyl polymer.

As a fourth aspect, in the hydrogel-forming material according to the first aspect, the disperse phase (A) further includes a polyhydric alcohol.

As a fifth aspect, in the hydrogel-forming material according to the first aspect, the disperse phase (B) including a water-soluble acidic polymer further includes a polyhydric alcohol.

As a sixth aspect, it relates to a method for producing a hydrogel comprising: a step of preparing the disperse phase (A) including a lipid peptide-based gelator, water, and a fatty acid salt as described in the first aspect; a step of adding the disperse phase (B) including a water-soluble acidic polymer to the disperse phase (A); and a step of stirring the resulting mixture at room temperature and then leaving the resulting mixture still standing to form a hydrogel.

As a seventh aspect, in the method for producing a hydrogel according to the seventh aspect, preparation of the disperse phase (A) is performed by mixing the lipid peptide-based gelator, water, and the fatty acid salt at a high temperature with stirring and then leaving the resulting mixture to cool to reach room temperature.

As an eighth aspect, it relates to a hydrogel formed from the hydrogel-forming material as described in any one of the first aspect to the fifth aspect.

As a ninth aspect, it relates to a premix useful in preparation of a hydrogel for use in a cosmetic or a quasi drug comprising: a lipid peptide-based gelator consisting of at least one of a compound of Formula (1) or a pharmaceutically usable salt thereof; water; and a fatty acid salt:

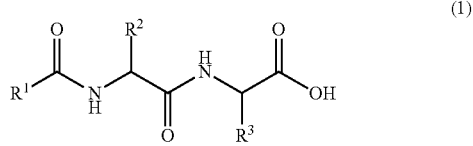
(1)

(where $R^1$ is a $C_{9-23}$ aliphatic group, $R^2$ is a hydrogen atom or a $C_{1-4}$ alkyl group that optionally has a $C_{1-2}$ branched chain, $R^3$ is a —$(CH_2)_n$—X group, n is a number of 1 to 4, X is an amino group, a guanidino group, a —$CONH_2$ group, a 5-membered ring optionally containing 1 to 3 nitrogen atom(s), a 6-membered ring optionally containing 1 to 3 nitrogen atom(s), or a condensed heterocycle that contains a 5-membered ring and a 6-membered ring optionally containing 1 to 3 nitrogen atom(s)).

Effects of the Invention

The hydrogel-forming material of the present invention is a binary system constituted of a disperse phase including a gelator and a fatty acid salt and a disperse phase including a water-soluble acidic polymer. Because of this, mixing the two phases (liquid phases) with stirring achieves an increase in viscosity, and an excellent hydrogel can be easily obtained without formation of insoluble matters or deposits just by leaving the resulting mixture still standing at room temperature. This can ensure safety and enhanced productivity due to reduction in cooling time when a hydrogel is produced in an industrial scale and can also provide a hydrogel-forming material that is improved in terms of operability, cost, and consistency in quality.

The lipid peptide-based gelator used in the present invention, when stirred with a particular fatty acid salt and water under relatively gentle conditions in terms of temperature, for example, at 80° C., can be dispersed in water serving as a medium in a relatively short time. In addition, when the resulting mixture is left to cool with stirring, it is not gelled but can be kept in a liquid state (a disperse phase) even at room temperature. Therefore, this disperse phase can be suitably used as a gel premix material that can be stored at room temperature.

In addition, the lipid peptide-based gelator included in the hydrogel-forming material of the present invention is a synthetic low-molecular compound that is solely composed of a lipid and a peptide and is highly safe. In addition, the fatty acid salt contained as an additive is an additive generally used in foods, cosmetics, and pharmaceuticals. In other words, the hydrogel-forming material and the premix of the present invention are highly safe for living organisms and extremely useful particularly in applications such as cell culture bases, biomedical materials, or cosmetics materials, when considering the high safety level of required in these applications.

Besides, the hydrogel-forming material and the premix of the present invention allow a gel to be formed by a gelation of water without using, for example, a crosslinking agent or the like that is necessary for forming a conventional synthetic polymer gel. Therefore, unreacted substances such as crosslinking agent are not left in the resulting hydrogel. In addition, the lipid peptide-based gelator included in the hydrogel-forming material and the premix allow a hydrogel to be formed when being added at an amount as small as about 1% by mass, for example, 0.1 to 0.5% by mass. Accordingly, a burden to the environment or living organisms is small when incorporated.

The method for producing a hydrogel of the present invention allows a hydrogel to be formed by stirring two types of liquids together under condition of room temperature. Therefore, the method is advantageous in terms of enhancement in productivity (due to reduction in cooling time) and production safety, which have been regarded as an issue when scaling up the production in the conventional processes that require high temperature condition, as well as in terms of cost. In addition, by the method of the present invention, a hydrogel can be formed without causing denaturation of additives used in cosmetics or quasi drugs, which are preferably kept away from heat. Further, since the system can be kept uniform by stirring, the method of the present invention is advantageous in terms of consistency in quality.

As described above, the hydrogel of the present invention can be obtained with a small amount of gelator used compared to conventional cases and therefore can be regarded as safe to living organisms and the environment.

As described above, a gel obtained from a lipid peptide that is a low-molecular compound can be readily decomposed in the outside environment, for example, by soil bacteria and the like when used in the soil or by metabolic enzymes when used in living organisms, Therefore, a burden to the environment or living organisms is small.

Further, the hydrogel of the present invention can be formed at room temperature as described above and can incorporate an additive that can be unfavorably affected by heat.

Besides, the hydrogel of the present invention is within the range of weakly acidic to neutral pH values and is therefore regarded as a gel having a pH within the range suitable for applications such as cell culture bases, biomedical materials, and cosmetics materials.

MODES FOR CARRYING OUT THE INVENTION

The present invention relates to a hydrogel-forming material that includes a disperse phase (A) including a lipid peptide-based gelator consisting of at least one of a compound of Formula (1) to be described below in detail or a pharmaceutically usable salt thereof, water, and a fatty acid salt and a disperse phase (B) that includes a water-soluble acidic polymer increasing viscosity by neutralization.

Each component will be described.

<Disperse Phase (A)>

[Lipid Peptide-Based Gelator]

The lipid peptide-based gelator used in the present invention can be a compound of Formula (1) (lipid peptide) or a pharmaceutically usable salt thereof (a low-molecular compound having a lipid moiety serving as a hydrophobic moiety and a peptide moiety serving as a hydrophilic moiety).

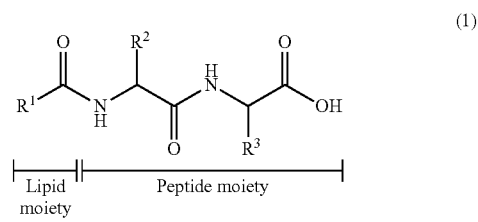

(1)

In Formula (1), $R^1$ is a $C_{9\text{-}23}$ aliphatic group and is preferably a linear $C_{11\text{-}23}$ aliphatic group that optionally contains 0 to 2 unsaturated bonds.

Specific examples of the lipid moiety (acyl group) including $R^1$ and an adjacent carbonyl group can include a lauroyl group, a dodecylcarbonyl group, a myristoyl group, a tetradecylcarbonyl group, a palmitoyl group, a margaroyl group, an oleoyl group, an elaidoyl group, a linoleoyl group, a stearoyl group, a vaccenoyl group, an octadecylcarbonyl group, an arachidoyl group, an eicosylcarbonyl group, a behenoyl group, an erucanoyl group, a docosylcarbonyl group, a lignoceroyl group, and a nervonoyl group. Particularly preferable examples thereof include a lauroyl group, a myristoyl group, a palmitoyl group, a margaroyl group, a stearoyl group, an oleoyl group, an elaidoyl group, and a behenoyl group.

In Formula (1), $R^2$ in the peptide moiety is a hydrogen atom or a $C_{1\text{-}4}$ alkyl group that optionally contains a $C_{1\text{-}2}$ branched chain.

The $C_{1\text{-}4}$ alkyl group that optionally contains a $C_{1\text{-}2}$ branched chain means an alkyl group that contains a $C_{1\text{-}4}$ main chain and optionally contains a $C_{1\text{-}2}$ branched chain, and specific examples thereof include a methyl group, an ethyl group, a n-propyl group, an isopropyl group, a n-butyl group, an isobutyl group, a sec-butyl group, and a tert-butyl group.

$R^2$ is preferably a hydrogen atom or a $C_{1\text{-}3}$ alkyl group that optionally contains a $C_1$ branched chain, and is more preferably a hydrogen atom.

The $C_{1\text{-}3}$ alkyl group that optionally contains a $C_1$ branched chain means an alkyl group that contains a $C_{1\text{-}3}$ main chain and optionally contains a $C_1$ branched chain, and specific examples thereof include a methyl group, an ethyl group, a n-propyl group, an isopropyl group, an isobutyl group, and a sec-butyl group. A methyl group, an isopropyl group, an isobutyl group, and a sec-butyl group are preferable.

In Formula (1), $R^3$ is a —$(CH_2)_n$—X group. In the —$(CH_2)_n$—X group, n is a number of 1 to 4, and X is an amino group, a guanidino group, a —$CONH_2$ group, a 5-membered ring group optionally containing 1 to 3 nitrogen atom(s), a 6-membered ring group optionally containing 1 to 3 nitrogen atom(s), or a condensed heterocycle group that contains a 5-membered ring and a 6-membered ring optionally containing 1 to 3 nitrogen atom(s).

In the —(CH$_2$)$_n$—X group as R$^3$, X is preferably an amino group, a guanidino group, a carbamoyl group (—CONH$_2$ group), a pyrrole group, an imidazole group, a pyrazole group, or an indole group, and is more preferably an imidazole group. In the —(CH$_2$)$_n$—X group, n is preferably 1 or 2 and is more preferably 1.

Accordingly, the —(CH$_2$)$_n$— group is preferably an aminomethyl group, a 2-aminoethyl group, a 3-aminopropyl group, a 4-aminobutyl group, a carbamoylmethyl group, a 2-carbamoylethyl group, a 3-carbamoylbutyl group, a 2-guanidinoethyl group, a 3-guanidinobutyl group, a pyrrole methyl group, a 4-imidazole methyl group, a pyrazole methyl group, or a 3-indole methyl group, is more preferably a 4-aminobutyl group, a carbamoylmethyl group, a 2-carbamoylethyl group, a 3-guanidinobutyl group, a 4-imidazole methyl group, or a 3-indole methyl group, and is further preferably a 4-imidazole methyl group.

Lipid peptides that are particularly preferable as the lipid peptide-based gelator in the compound of Formula (1) are the following compounds formed from a lipid moiety and a peptide moiety (a moiety of assembled amino acids) (amino acid abbreviations are as follows: alanine (Ala), asparagine (Asn), glutamine (Gln), glycine (Gly), histidine (His), isoleucine (Ile), leucine (Leu), lysine (Lys), tryptophan (Trp), and valine (Val)): lauroyl-Gly-His, lauroyl-Gly-Gln, lauroyl-Gly-Asn, lauroyl-Gly-Trp, lauroyl-Gly-Lys, lauroyl-Ala-His, lauroyl-Ala-Gln, lauroyl-Ala-Asn, lauroyl-Ala-Trp, and lauroyl-Ala-Lys; myristoyl-Gly-His, myristoyl-Gly-Gln, myristoyl-Gly-Asn, myristoyl-Gly-Trp, myristoyl-Gly-Lys, myristoyl-Ala-His, myristoyl-Ala-Gln, myristoyl-Ala-Asn, myristoyl-Ala-Trp, and myristoyl-Ala-Lys; palmitoyl-Gly-His, palmitoyl-Gly-Gln, palmitoyl-Gly-Asn, palmitoyl-Gly-Trp, palmitoyl-Gly-Lys, palmitoyl-Ala-His, palmitoyl-Ala-Gln, palmitoyl-Ala-Asn, palmitoyl-Ala-Trp, and palmitoyl-Ala-Lys; and stearoyl-Gly-His, stearoyl-Gly-Gln, stearoyl-Gly-Asn, stearoyl-Gly-Trp, stearoyl-Gly-Lys, stearoyl-Ala-His, stearoyl-Ala-Gln, stearoyl-Ala-Asn, stearoyl-Ala-Trp, and stearoyl-Ala-Lys.

Most preferable examples thereof include lauroyl-Gly-His and lauroyl-Ala-His; myristoyl-Gly-His and myristoyl-Ala-His; palmitoyl-Gly-His and palmitoyl-Ala-His; and stearoyl-Gly-His and stearoyl-Ala-His.

In the present invention, the ratio of the lipid peptide-based gelator to be added is, for example, 0.01 to 30% by mass, preferably 0.02 to 10 percent by mass, and more preferably 0.05 to 5 percent by mass relative to the total mass of the hydrogel.

The lipid peptide-based gelator used in the present invention contains at least one of the compound of Formula (1) (lipid peptide) or a pharmaceutically usable salt thereof, and such a compound can be used alone or as a combination of two or more of these as a hydrogelator.

[Fatty Acid Salt]

The fatty acid salt used in the present invention can be a fatty acid salt that is generally used as an additive in cosmetics and/or pharmaceuticals.

Examples of the fatty acid salt include butyrates, valerates, caproates, enanthates, caprylates, pelargonates, caprates, laurates, myristates, pentadecylates, palmitates, palmitoleates, margarates, stearates, oleates, vaccenates, linoleates, (9,12,15)-linolenates, (6,9,12)-linolenates, eleostearates, tuberculostearates, arachidates, arachidonates, behenates, lignocerates, nervonates, cerotates, montanates, and melissates. Laurates, myristates, palmitates, stearates, and oleates are preferable and myristates, palmitates, and stearates are further preferable.

The fatty acid salt is a sodium salt or a potassium salt, for example, and is particularly preferably a sodium salt.

In the present invention, the ratio of the fatty acid salt to be added is, for example, 0.01 to 30% by mass, preferably 0.02 to 10 percent by mass, and more preferably 0.05 to 2 percent by mass relative to the total mass of the hydrogel.

The fatty acid salt used in the present invention contains at least one type selected from the group consisting of the fatty acid salts exemplified above, and such fatty acid salts can be used alone or as a combination of two or more of these.

[Preparation of Disperse Phase (A)]

The disperse phase (A) can be produced by mixing the lipid peptide-based gelator containing at least one of the compound of Formula (1) or a pharmaceutically usable salt thereof, water, and the fatty acid salt and then stirring the resulting mixture under conditions in which the temperature is high, for example, at room temperature or higher and lower than 100° C., preferably at 50° C. to 90° C., and more preferably at 60° C. to 80° C., followed by leaving the resulting mixture to cool with stirring to near room temperature.

The duration of the heating and stirring varies depending on the types and the amounts of the lipid peptide-based gelator and an additive to be added, and is usually about 20 minutes to about 90 minutes.

During the cooling process with stirring, an additive for cosmetics and/or an additive for quasi drugs to be described below can be added as desired. Among them, a polyhydric alcohol such as polyols and polymers thereof, for example, glycerin, 1,3-butylene glycol, propylene glycol, 3-methyl-1,3-butanediol, 1,3-propanediol, 2-methyl-1,3-propanediol, trimethylolpropane, pentaerythritol, hexylene glycol, diglycerin, polyglycerin, diethylene glycol, polyethylene glycol, dipropylene glycol, polypropylene glycol, and ethylene glycol-propylene glycol copolymers can be preferably added.

The disperse phase (A) including the lipid peptide-based gelator, the fatty acid salt, and water is suitably used as a gel premix material that can be stored at room temperature, and can be suitably used, for example, as a premix for preparation of cosmetics and quasi drugs, in other words, a premix material for preparation of a gel to be used in cosmetics and quasi drugs. In this premix, various additives that are well known as additives for cosmetics and/or quasi drugs, which are to be described below, can also be added. Such a premix is also within the scope of the present invention.

<Disperse Phase (B) Including Water-Soluble Acidic Polymer>

The disperse phase (B) including a water-soluble acidic polymer as a constituent of the hydrogel-forming material of the present invention, when mixed with the disperse phase (A), undergoes neutralization to make the pH of the system neutral and weakly acidic and also increase the viscosity of the system, causing gelation of the system. This enables hydrogel preparation to be performed at room temperature with stirring.

Examples of the disperse phase including an acidic polymer include a disperse phase of polyacrylic acid and a carboxyvinyl polymer. The polyacrylic acid may be an acrylic acid homopolymer, an acrylic acid-methacrylic acid ester copolymer, or an acrylic acid-alkyl methacrylate copolymer.

The polyacrylic acid may be used alone or can be used as a combination of two or more of these.

In the present invention, the concentration of the polyacrylic acid or the carboxyvinyl polymer as a constituent of the disperse phase including an acidic polymer is, for example, 0.001 to 10% by mass, preferably 0.005 to 5 percent by mass, and more preferably 0.01 to 2 percent by mass relative to the total mass of the resulting hydrogel.

To the disperse phase (B) including an acidic polymer, an additive for cosmetics and/or quasi drugs, which is to be described below, can be formulated. Among them, a polyhydric alcohol such as polyols and polymers thereof, for example, glycerin, 1,3-butylene glycol, propylene glycol, 3-methyl-1,3-butanediol, 1,3-propanediol, 2-methyl-1,3-propanediol, trimethylolpropane, pentaerythritol, hexylene glycol, diglycerin, polyglycerin, diethylene glycol, polyethylene glycol, dipropylene glycol, polypropylene glycol, and ethylene glycol-propylene glycol copolymers can be preferably added.

[Other Additives]

To the gel-forming material of the present invention (the disperse phase (A), the disperse phase (B) including an acidic polymer), an additive generally usable as an additive for cosmetics and an additive for quasi drugs can be added where appropriate. Examples of additional ingredients such as physiologically active substances and functional substances formulated in external skin preparations such as cosmetics and quasi drugs include oily base materials, moisturizers, tactile-feeling enhancers, surfactants, polymers, thickeners and gelators, solvents, propellants, antioxidants, reducing agents, oxidizing agents, preservatives, antimicrobial agents, antiseptics, chelating agents, pH-adjusters, acids, alkalis, powders, inorganic salts, ultraviolet absorbers, skin-brightening agents, vitamins and derivatives thereof, hair growth-promoting agents, blood circulation-promoters, stimulating agents, hormones, anti-wrinkle agents, anti-aging agents, tightening agents, cool-feeling agents, warm-feeling agents, wound-healing promoters, abirritants, analgesics, cell activators, plant, animal, and microbial extracts, antipruritics, keratin-exfoliating/dissolving agents, antiperspirants, refrigerants, styptics, enzymes, nucleic acids, perfumes, coloring agents, colorants, dyes, pigments, antiphlogistics, anti-inflammatory agents, anti-asthmatic agents, drugs for chronic obstructive pulmonary diseases, antiallergic agents, immunomodulators, anti-infective agents, and antifungal agents.

These additional ingredients are exemplified below. Preferable examples of the oily base materials include higher (polyhydric) alcohols such as cetanol, myristyl alcohol, oleyl alcohol, lauryl alcohol, cetostearyl alcohol, stearyl alcohol, arachyl alcohol, behenyl alcohol, jojoba alcohol, chimyl alcohol, selachyl alcohol, batyl alcohol, hexyldecanol, isostearyl alcohol, 2-octyldodecanol, and dimer diols; aralkyl alcohols such as benzyl alcohol, and derivatives thereof; higher fatty acids such as lauric acid, myristic acid, palmitic acid, stearic acid, isostearic acid, behenic acid, undecylene acid, 12-hydroxystearic acid, palmitoleic acid, oleic acid, linoleic acid, linolenic acid, erucic acid, docosahexaenoic acid, eicosapentaenoic acid, isohexadecanoic acid, anteisoheneicosanoic acid, branched long-chain fatty acids, dimer acids, and hydrogenated dimer acids, metal soaps thereof such as aluminum salts thereof, calcium salts thereof, magnesium salts thereof, zinc salts thereof, potassium salts thereof, and sodium salts thereof, and nitrogen-containing derivatives thereof such as amides thereof; hydrocarbons such as liquid paraffin (mineral oil), heavy liquid isoparaffin, light liquid isoparaffin, α-olefin oligomers, polyisobutene, hydrogenated polyisobutene, polybutene, squalane, olive squalane, squalene, petrolatum, and solid paraffin; waxes such as candelilla wax, carnauba wax, rice wax, Japan wax, beeswax, montan wax, ozokerite, ceresin, paraffin wax, microcrystalline wax, petrolatum, Fischer-Tropsch Wax, polyethylene wax, and ethylene-propylene copolymers; vegetable oils such as coconut oil, palm oil, palm kernel oil, safflower oil, olive oil, castor oil, avocado oil, sesame seed oil, tea oil, evening primrose oil, wheat germ oil, macadamia oil, hazelnut oil, kukui nut oil, rose hip oil, meadowfoam oil, persic oil, tea tree oil, mint oil, maize oil, rape oil, sunflower oil, wheat germ oil, linseed oil, cottonseed oil, soybean oil, peanut oil, rice bran oil, cocoa butter, shea butter, hydrogenated coconut oil, hydrogenated castor oil, jojoba oil, and hydrogenated jojoba oil; animal oils/fats such as beef tallow, milk fat, horse fat, egg-yolk oil, mink oil, and turtle oil; animal waxes such as spermaceti, lanolin, and orange roughy oil; lanolins such as liquid lanolin, reduced lanolin, adsorption-purified lanolin, acetylated lanolin, acetylated liquid lanolin, hydroxylated lanolin, polyoxyethylene lanolin, lanolin acid, hard lanolin acid, lanolin alcohol, acetylated lanolin alcohol, and acetylated (cetyl/lanolyl) ester; phospholipids such as lecithin, phosphatidylcholine, phosphatidylethanolamine, phosphatidylserine, phosphatidylglycerol, phosphatidylinositol, sphingophospholipids including sphingomyelin, phosphatidic acid, and lysolecithin; phospholipid derivatives such as hydrogenated soy phospholipid, partially hydrogenated soy phospholipid, hydrogenated egg-yolk phospholipid, and partially hydrogenated egg-yolk phospholipid; sterols such as cholesterol, dihydrocholesterol, lanosterol, dihydrolanosterol, phytosterol, and cholic acid; sapogenins; saponins; sterol esters such as cholesteryl acetate, cholesteryl nonanoate, cholesteryl stearate, cholesteryl isostearate, cholesteryl oleate, di(cholesteryl/behenyl/octyldodecyl) N-lauroyl-L-glutamate, di(cholesteryl/octyldodecyl) N-lauroyl-L-glutamate, di(phytosteryl/behenyl/octyldodecyl) N-lauroyl-L-glutamate, di(phytosteryl/octyldodecyl) N-lauroyl-L-glutamate, acyl sarcosine alkyl esters including isopropyl N-lauroyl sarcosinate, cholesteryl 12-hydroxystearate, cholesteryl macadamiate, phytosteryl macadamiate, phytosteryl isostearate, soft lanolin acid cholesteryl ester, hard lanolin acid cholesteryl ester, branched long-chain fatty acid cholesteryl esters, and long-chain α-hydroxy fatty acid cholesteryl esters; lipid complexes such as phospholipid-cholesterol complexes and phospholipid-phytosterol complexes; monoalcohol carboxylic acid esters such as octyldodecyl myristate, hexyldecyl myristate, octyldodecyl isostearate, cetyl palmitate, octyldodecyl palmitate, cetyl octanoate, hexyldecyl octanoate, isotridecyl isononanoate, isononyl isononanoate, octyl isononanoate, isotridecyl isononanoate, isodecyl neopentanoate, isotridecyl neopentanoate, isostearyl neopentanoate, octyldodecyl neodecanoate, oleyl oleate, octyldodecyl oleate, octyldodecyl ricinoleate, octyldodecyl lanolate, hexyldecyl dimethyloctanoate, octyldodecyl erucate, hydrogenated castor oil isostearate, ethyl oleate, ethyl avocadate, isopropyl myristate, isopropyl palmitate, octyl palmitate, isopropyl isostearate, isopropyl lanolate, diethyl sebacate, diisopropyl sebacate, dioctyl sebacate, diisopropyl adipate, dibutyloctyl sebacate, diisobutyl adipate, dioctyl succinate, and triethyl citrate; oxyacid esters such as cetyl lactate, diisostearyl malate, and hydrogenated castor oil monoisostearate; polyhydric alcohol fatty acid esters such as glyceryl trioctanoate, glyceryl trioleate, glyceryl triisostearate, glyceryl diisostearate, caprylic/capric triglyceride, caprylic/capric/myristic/stearic triglyceride, hydrogenated rosin triglyceride (hydrogenated ester gum), rosin triglyceride (ester gum), glyceryl behenate eicosanedioate, trimethylolpropane trioctanoate, trimethylolpropane triisostearate, neopentyl glycol dioctanoate, neopentyl glycol dicaprate, 2-butyl-2-ethyl-1,3-propanediol dioctanoate, propylene glycol dioleate, pentaerythrityl tetraoctanoate, pentaerythrityl hydrogenated rosinate, ditrimethylolpropane triethylhexanoate, ditrimethylolpropane (isostearate/sebacate), pentaerythrityl triethylhexanoate, dipentaerythrityl (hydroxystearate/stearate/resinate), diglyceryl diisostearate, polyglyceryl tetraisostearate, polyglyceryl-10 nonaisostearate, polyglyceryl-8 deca(erucate/isostearate/ricinoleate), (hexyldecanoic acid/sebacic acid) diglyceryl oligoester, glycol distearate (ethylene glycol distearate), 3-methyl-1,5-pentanediol dineopentanoate, and 2,4-diethyl-1,5-pentanediol dineopentanoate; dimer acid derivatives or dimer diol derivatives such as diisopropyl dimer dilinoleate, diisostearyl dimer dilinoleate, di(isostearyl/phytosteryl) dimer dilinoleate, (phytosteryl/behenyl) dimer dilinoleate, (phytosteryl/isostearyl/cetyl/stearyl/behenyl) dimer dilinoleate, dimer dilinoleyl dimer dilinoleate, dimer dilinoleyl diisostearate, dimer dilinoleyl hydrogenated rosin condensates, hydrogenated castor oil dimer dilinoleate, and hydroxyalkyl dimer dilinoleyl ether; fatty acid alkanolamides such as coconut fatty acid monoethanolamide (cocamide MEA), coconut fatty acid diethanolamide (cocamide DEA), lauric acid monoethanolamide (lauramide MEA), lauric acid diethanolamide (lauramide DEA), lauric acid monoisopropanolamide (lauramide MIPA), palmitic acid monoethanolamide (palmitamide MEA), palmitic acid diethanolamide (palmitamide DEA), and coconut fatty acid methylethanolamide (cocamide methyl MEA); silicones such as dimethicone (dimethylpolysiloxane), highly-polymerized dimethicone (highly-polymerized dimethylpolysiloxane), cyclomethicone (cyclic dimethylsiloxane, decamethylcyclopentasiloxane), phenyl trimethicone, diphenyl dimethicone, phenyl dimethicone, stearoxypropyldimethylamine, (aminoethylaminopropyl methicone/dimethicone) copolymer, dimethiconol, dimethiconol crosspolymer, silicone resins, silicone rubber, amino-modified silicones including aminopropyl dimethicone and amodimethicone, cation-modified silicones, polyether-modified silicones including dimethicone copolyols, polyglycerin-modified silicones, sugar-modified silicones, carboxylic acid-modified silicones, phosphoric acid-modified silicones, sulfuric acid-modified silicones, alkyl-modified silicones, fatty acid-modified silicones, alkyl ether-modified silicones, amino acid-modified silicones, peptide-modified silicones, fluorine-modified silicones, cation-modified and polyether-modified silicones, amino-modified and polyether-modified silicones, alkyl-modified and polyether-modified silicones, and polysiloxane-oxyalkylene copolymers; and fluorine oils such as perfluorodecane, perfluorooctane, and perfluoropolyether.

Preferable examples of the moisturizers and the tactile-feeling enhancers include polyols and polymers thereof such as glycerin, 1,3-butylene glycol, propylene glycol, 3-methyl-1,3-butanediol, 1,3-propanediol, 2-methyl-1,3-propanediol, trimethylolpropane, pentaerythritol, hexylene glycol, diglycerin, polyglycerin, diethylene glycol, polyethylene glycol, dipropylene glycol, polypropylene glycol, and ethylene glycol-propylene glycol copolymers; glycol alkyl ethers such as diethylene glycol monoethyl ether (ethoxydiglycol), ethylene glycol monoethyl ether, ethylene glycol monobutyl ether, and diethylene glycol dibutyl ether; water-soluble esters such as polyglyceryl-10 (eicosanedioate/tetradecanedioate) and polyglyceryl-10 tetradecanedioate; sugar alcohols such as sorbitol, xylitol, erythritol, mannitol, and maltitol; saccharides and derivatives thereof such as glucose, fructose, galactose, mannose, threose, xylose, arabinose, fucose, ribose, deoxyribose, maltose, trehalose, lactose, raffinose, gluconic acid, glucuronic acid, cyclodextrins ($\alpha$-, $\beta$-, and $\gamma$-cyclodextrins, and modified cyclodextrins such as maltosyl cyclodextrin and hydroxyalkyl cyclodextrin), $\beta$-glucan, chitin, chitosan, heparin and heparin derivatives, pectin, arabinogalactan, dextrin, dextran, glycogen, ethyl glucoside, poly(glucosylethyl methacrylate), and (glucosylethyl methacrylate) copolymer; hyaluronic acid and sodium hyaluronate; sodium chondroitin sulfate; mucoitin sulfate, charonin sulfate, kerato sulfate, and dermatan sulfate; *Tremella fuciformis* extract and *Tremella fuciformis* polysaccharide; fucoidan; tuberose polysaccharide and natural polysaccharides; organic acids such as citric acid, tartaric acid, and lactic acid, and salts thereof; urea and derivatives thereof; 2-pyrrolidone-5-carboxylic acid, and salts thereof including sodium thereof; amino acids such as betaine (trimethylglycine), proline, hydroxyproline, arginine, lysine, serine, glycine, alanine, phenylalanine, tyrosine, $\beta$-alanine, threonine, glutamic acid, glutamine, asparagine, aspartic acid, cysteine, cysteine, methionine, leucine, isoleucine, valine, tryptophan, histidine, and taurine, and salts thereof; protein peptides, and derivative thereof, such as collagen, fish collagen, atelocollagen, gelatin, elastin, peptides derived from decomposed collagen, hydrolyzed collagen, hydroxypropylammonium chloride hydrolyzed collagen, peptides derived from decomposed elastin, peptides derived from decomposed keratin, hydrolyzed keratin, peptides derived from decomposed conchiolin, hydrolyzed conchiolin, peptides derived from decomposed silk protein, hydrolyzed silk, sodium lauroyl hydrolyzed silk, peptides derived from decomposed soy protein, peptides derived from decomposed wheat protein, hydrolyzed wheat protein, peptides derived from decomposed casein, and acylated peptides; acylated peptides such as palmitoyl oligopeptide, palmitoyl pentapeptide, and palmitoyl tetrapeptide; silylated peptides; a culture medium of lactic acid bacteria, a yeast extract solution, an eggshell membrane protein, bovine submaxillary mucin, hypotaurine, sesame lignan glycoside, glutathione, albumin, and whey; choline chloride and phosphoryl choline; and animal and plant extract components such as a placenta extract solution, elastin, collagen, aloe extract, *Hamamelis virginiana* water, *Luffa cylindrica* water, *Chamomilla recutita* extract, licorice extract, *Symphytum officinale* extract, silk extract, *Rosa roxburghii* extract, *Achillea millefolium* extract, *Eucalyptus globulus* extract, and *Melilotus officinalis* extract, and ceramides such as natural ceramides (type 1, 2, 3, 4, 5, and 6), hydroxyceramide, pseudoceramide, sphingoglycolipid, ceramide-containing extracts, and glucosylceramide-containing extracts.

Preferable examples of the surfactants include anionic surfactants, nonionic surfactants, cationic surfactants, amphoteric surfactants, and polymer surfactants. Preferable examples of the surfactants are exemplified below. Preferable examples of the anionic surfactants include fatty acid salts such as sodium laurate, sodium myristate, sodium palmitate, sodium stearate, potassium laurate, and potassium myristate; alkyl sulfuric acid ester salts such as sodium lauryl sulfate, triethanolamine lauryl sulfate, and ammonium lauryl sulfate; polyoxyethylene alkyl sulfates such as sodium laureth sulfate and triethanolamine laureth sulfate; acyl N-methyl amino acid salts such as sodium cocoyl methyl taurate, potassium cocoyl methyl taurate, sodium lauroyl methyl taurate, sodium myristoyl methyl taurate, sodium lauroyl methylalaninate, sodium lauroyl sarcosinate, triethanolamine lauroyl sarcosinate, and sodium lauroyl glutamate methylalaninate; acylamino acid salts such as sodium cocoyl glutamate, triethanolamine cocoyl glutamate, sodium lauroyl glutamate, sodium myristoyl glutamate, sodium stearoyl glutamate, ditriethanolamine palmitoyl aspartate, and triethanolamine cocoyl alaninate; polyoxyethylene alkyl ether acetates such as sodium laureth acetate; succinic acid ester salts such as sodium lauroyl monoethanolamide succinate; fatty acid alkanolamide ether carboxylates; acyl lactates; polyoxyethylene fatty amine sulfates; fatty acid alkanolamide sulfates; fatty acid glyceride sulfates such as sodium glycerin hydrogenated coconut fatty acid sulfate; alkylbenzene polyoxyethylene sulfates; olefin sulfonates such as sodium α-olefin sulfonate; alkyl sulfosuccinates such as disodium lauryl sulfosuccinate and sodium dioctyl sulfosuccinate; alkyl ether sulfosuccinates such as disodium laureth sulfosuccinate, sodium monolauroyl monoethanolamide polyoxyethylene sulfosuccinate, and sodium lauryl polypropylene glycol sulfosuccinate; alkylbenzene sulfonates such as sodium tetradecylbenzene sulfonate and triethanolamine tetradecylbenzene sulfonate; alkyl naphthalene sulfonates; alkane sulfonates; α-sulfofatty acid methyl ester salts; acyl isethionates; alkyl glycidyl ether sulfonates; alkyl sulfoacetates; alkyl ether phosphoric acid ester salts such as sodium laureth phosphate, sodium dilaureth phosphate, sodium trilaureth phosphate, and sodium monoreth phosphate; alkyl phosphoric acid ester salts such as potassium lauryl phosphate; sodium caseinate; alkyl aryl ether phosphates; fatty amide ether phosphates; phospholipids such as phosphatidylglycerol, phosphatidylinositol, and phosphatidic acid; and silicone anionic surfactants such as carboxylic acid-modified silicones, phosphoric acid-modified silicones, and sulfuric acid-modified silicones. Preferable examples of the nonionic surfactants include polyoxyethylene alkyl ethers with various numbers of polyoxyethylenes addition such as laureths (polyoxyethylene lauryl ethers), ceteths (polyoxyethylene cetyl ethers), steareths (polyoxyethylene stearyl ethers), beheneths (polyoxyethylene behenyl ethers), isosteareths (polyoxyethylene isostearyl ethers), and octyldodeceths (polyoxyethylene octyldodecyl ethers); polyoxyethylene alkyl phenyl ethers; castor oil derivatives and hydrogenated castor oil derivatives such as polyoxyethylene hydrogenated castor oil, polyoxyethylene castor oil, polyoxyethylene hydrogenated castor oil monoisostearate, polyoxyethylene hydrogenated castor oil triisostearate, polyoxyethylene hydrogenated castor oil monopyroglutamate monoisostearate diester, and polyoxyethylene hydrogenated castor oil maleate; polyoxyethylene phytosterol; polyoxyethylene cholesterol; polyoxyethylene cholestanol; polyoxyethylene lanolin; polyoxyethylene reduced lanolin; polyoxyethylene-polyoxypropylene alkyl ethers such as polyoxyethylene-polyoxypropylene cetyl ether, polyoxyethylene-polyoxypropylene 2-decyltetradecyl ether, polyoxyethylene-polyoxypropylene monobutyl ether, polyoxyethylene-polyoxypropylene hydrogenated lanolin, and polyoxyethylene-polyoxypropylene glycerin ether; polyoxyethylene-polyoxypropylene glycol; (poly)glycerin polyoxypropylene glycols such as PPG-9 diglyceryl; glycerin fatty acid partial esters such as glyceryl stearate, glyceryl isostearate, glyceryl palmitate, glyceryl myristate, glyceryl oleate, glyceryl cocoate, glycerin mono-cottonseed oil fatty acid, glycerin monoerucate, glycerin sesquioleate, glycerin α,α'-oleate pyroglutamate, and glycerin monostearate malate; polyglycerin fatty acid esters such as polyglyceryl-2 stearate, polyglyceryl-3 stearate, polyglyceryl-4 stearate, polyglyceryl-5 stearate, polyglyceryl-6 stearate, polyglyceryl-8 stearate, polyglyceryl-10 stearate, polyglyceryl-6 distearate, polyglyceryl-10 distearate, polyglyceryl-2 tristearate, polyglyceryl-10 decastearate, polyglyceryl-2 isostearate, polyglyceryl-3 isostearate, polyglyceryl-4 isostearate, polyglyceryl-5 isostearate, polyglyceryl-6 isostearate, polyglyceryl-8 isostearate, polyglyceryl-10 isostearate, polyglyceryl-2 diisostearate (diglyceryl diisostearate), polyglyceryl-3 diisostearate, polyglyceryl-10 diisostearate, polyglyceryl-2 triisostearate, polyglyceryl-2 tetraisostearate, polyglyceryl-10 decaisostearate, polyglyceryl-2 oleate, polyglyceryl-3 oleate, polyglyceryl-4 oleate, polyglyceryl-5 oleate, polyglyceryl-6 oleate, polyglyceryl-8 oleate, polyglyceryl-10 oleate, polyglyceryl-6 dioleate, polyglyceryl-2 trioleate, and polyglyceryl-10 decaoleate; ethylene glycol mono-fatty acid esters such as ethylene glycol monostearate; propylene glycol mono-fatty acid esters such as propylene glycol monostearate; pentaerythritol fatty acid partial esters; sorbitol fatty acid partial esters; maltitol fatty acid partial esters; maltitol ether; sorbitan fatty acid esters such as sorbitan monooleate, sorbitan monoisostearate, sorbitan monolaurate, sorbitan monopalmitate, sorbitan monostearate, sorbitan sesquioleate, sorbitan trioleate, sorbitan penta-2-ethylhexylate diglycerol, and sorbitan tetra-2-ethylhexylate diglycerol; sugar derivative partial esters such as sucrose fatty acid esters, methyl glucoside fatty acid esters, and trehalose undecylenoate; alkyl glucosides such as caprylyl glucoside; alkyl polyglycosides; lanolin alcohol; reduced lanolin; polyoxyethylene fatty acid monoesters and polyoxyethylene fatty acid diesters such as polyoxyethylene distearate, polyethylene glycol diisostearate, polyoxyethylene monooleate, and polyoxyethylene dioleate; polyoxyethylene-propylene glycol fatty acid esters; polyoxyethylene glycerin fatty acid esters such as polyoxyethylene glycerin monostearate, polyoxyethylene glycerin monoisostearate, and polyoxyethylene glycerin triisostearate; polyoxyethylene sorbitan fatty acid esters such as polyoxyethylene sorbitan monooleate, polyoxyethylene sorbitan monostearate, polyoxyethylene sorbitan monooleate, and polyoxyethylene sorbitan tetraoleate; polyoxyethylene sorbitol fatty acid esters such as polyoxyethylene sorbitol monolaurate, polyoxyethylene sorbitol monooleate, polyoxyethylene sorbitol pentaoleate, and polyoxyethylene sorbitol monostearate; polyoxyethylene methyl glucoside fatty acid esters; polyoxyethylene alkyl ether fatty acid esters; polyoxyethylene-modified animal and vegetable oils/fats such as polyoxyethylene sorbitol beeswax; alkyl glyceryl ethers such as isostearyl glyceryl ether, chimyl alcohol, selachyl alcohol, and batyl alcohol; polyhydric alcohol alkyl ethers; polyoxyethylene alkylamines; tetrapolyoxyethylene/tetrapolyoxypropylene-ethylenediamine condensates; natural surfactants such as saponins and sophorolipid; polyoxyethylene fatty acid amides; fatty acid alkanolamides such as coconut fatty acid monoethanolamide (cocamide MEA), coconut fatty acid diethanolamide (cocamide DEA), lauric acid monoethanolamide (lauramide MEA), lauric acid diethanolamide (lauramide DEA), lauric acid monoisopropanolamide (lauramide MIPA), palmitic acid monoethanolamide (palmitamide MEA), palmitic acid diethanolamide (palmitamide DEA), and coconut fatty acid methylethanolamide (cocamide methyl MEA); alkyl dimethylamine oxides such as lauramine oxide, cocamine oxide, stearamine oxide, and behenamine oxide; alkyl ethoxy dimethylamine oxides; polyoxyethylene alkyl mercaptans; and silicone nonionic surfactants such as polyether-modified silicones including dimethicone copolyols, polysiloxane-oxyalkylene copolymers, polyglycerin-modified silicones, and sugar-modified silicones. Preferable examples of the cationic surfactants include alkyl trimethylammonium chlorides such as behentrimonium chloride, steartrimonium chloride, cetrimonium chloride, and lauryltrimonium chloride; alkyl trimethylammonium bromides such as stearyltrimonium bromide; dialkyl dimethylammonium chlorides such as distearyldimonium chloride and dicocodimonium chloride; fatty acid amide amines such as stearamide propyldimethylamine and stearamide ethyldiethylamine, and salts thereof; alkyl ether amines such as stearoxypropyldimethylamine, and salts and quaternary salts thereof; fatty acid amide quaternary ammonium salts such as branched long-chain fatty acid (12 to 31) aminopropylethyldimethylammonium ethyl sulfates and lanolin fatty acid aminopropylethyldimethylammonium ethyl sulfate; polyoxyethylene alkylamines, and salts and quaternary salts thereof; alkylamine salts; fatty acid amide guanidium salts; alkyl ether ammonium salts; alkyl trialkylene glycol ammonium salts; benzalkonium salts; benzethonium salts; pyridinium salts such as cetylpyridinium chloride; imidazolinium salts; alkyl isoquinolinium salts; dialkyl morpholinium salts; polyamine fatty acid derivatives; and silicone cationic surfactants such as amino-modified silicones including aminopropyl dimethicone and amodimethicone, cation-modified silicones, cation-modified and polyether-modified silicones, and amino-modified and polyether-modified silicones. Preferable examples of the amphoteric surfactants include N-alkyl-N,N-dimethylamino acid betaines such as lauryl betaine (lauryl dimethylaminoacetic acid betaine); fatty acid amide alkyl-N,N-dimethylamino acid betaines such as cocamide propyl betaine and lauramide propyl betaine; imidazoline-type betaines such as sodium cocoamphoacetate and sodium lauroamphoacetate; alkyl sulfobetaines such as alkyl dimethyltaurines; sulfuric acid-type betaines such as alkyl dimethylamino ethanol sulfuric acid esters; phosphoric acid-type betaines such as alkyl dimethylamino ethanol phosphoric acid esters; phospholipids such as phosphatidylcholine, phosphatidylethanolamine, phosphatidylserine, sphingophospholipids including sphingomyelin, lysolecithin, hydrogenated soy phospholipid, partially hydrogenated soy phospholipid, hydrogenated egg-yolk phospholipid, partially hydrogenated egg-yolk phospholipid, and hydroxylated lecithin; and silicone amphoteric surfactants. Preferable examples of the polymer surfactants include polyvinyl alcohol, sodium alginate, starch derivatives, tragacanth gum, and acrylic acid-alkyl methacrylate copolymers; and various silicone surfactants.

Preferable examples of the polymers, the thickeners, and the gelators include guar gum, locust bean gum, quince seed, carrageenan, galactan, gum arabic, tara gum, tamarind, furcellaran, karaya gum, *Abelmoschus manihot*, cara gum, tragacanth gum, pectin, pectic acid and salts thereof including a sodium salt thereof, alginic acid and salts thereof including a sodium salt thereof, and mannan; starches such as rice starch, corn starch, potato starch, and wheat starch; xanthan gum, dextran, succinoglucan, curdlan, hyaluronic acid and salts thereof, xanthan gum, pullulan, gellan gum, chitin, chitosan, agar, brown algae extract, chondroitin sulfate, casein, collagen, gelatin, and albumin; cellulose and derivatives thereof such as methylcellulose, ethylcellulose, hydroxyethylcellulose, hydroxypropylcellulose, hydroxypropyl methylcellulose, carboxymethylcellulose and salts thereof including sodium thereof, methylhydroxypropylcellulose, sodium cellulose sulfate, dialkyl dimethylammonium sulfate cellulose, crystalline cellulose, and cellulose powder; starch derivatives such as soluble starch, starch polymers including carboxymethyl starch, methylhydroxypropyl starch, and methyl starch, starch hydroxypropyltrimonium chloride, and aluminum corn starch octenylsuccinate; alginic acid derivatives such as sodium alginate and propylene glycol alginic acid ester; polyvinylpyrrolidone (PVP), polyvinyl alcohol (PVA), vinylpyrrolidone-vinyl alcohol copolymers, and polyvinyl methyl ether; polyethylene glycol, polypropylene glycol, and polyoxyethylene-polyoxypropylene copolymers; amphoteric methacrylic acid ester copolymers such as (methacryloyloxyethylcarboxy betaine/alkyl methacrylate) copolymers and (acrylate/stearyl acrylate/ethylamine oxide methacrylate) copolymers; (dimethicone/vinyl dimethicone) crosspolymer, (alkyl acrylate/diacetone acrylamide) copolymer, and (alkyl acrylate/diacetone acrylamide) copolymer AMP; partially-saponified polyvinyl acetate and maleic acid copolymers; vinylpyrrolidone-dialkyl aminoalkyl methacrylate copolymers; acrylic resin alkanolamines; polyesters and water-dispersable polyesters; polyacrylamides; polyacrylic acid ester copolymers such as ethyl polyacrylate, carboxyvinyl polymers, polyacrylic acid and salts thereof including a sodium salt thereof, acrylic acid-methacrylic acid ester copolymers; acrylic acid-alkyl methacrylate copolymers; cationized celluloses such as polyquaternium-10, diallyldimethylammonium chloride-acrylamide copolymers such as polyquaternium-7, acrylic acid-diallyldimethylammonium chloride copolymers such as polyquaternium-22, acrylic acid-diallyldimethylammonium chloride-acrylamide copolymers such as polyquaternium-39, acrylic acid-cationized methacrylic acid ester copolymers, acrylic acid-cationized methacrylic acid amide copolymers, acrylic acid-methyl acrylate-methacrylamide propyltrimethylammonium chloride copolymers such as polyquaternium-47, and methacryloyl chloride choline ester polymers; cationized polysaccharides such as cationized oligosaccharides, cationized dextran, and guar hydroxypropyltrimonium chloride; polyethyleneimines; cationic polymers; polymers of 2-methacryloyloxyethylphosphorylcholine such as polyquaternium-51, and copolymers thereof with butyl methacrylate copolymer and the like; polymer emulsions such as acrylic resin emulsions, ethyl polyacrylate emulsions, polyacrylic alkyl ester emulsions, polyvinyl acetate resin emulsions, natural rubber latex, and synthetic latex; nitrocellulose; polyurethanes and various copolymers thereof; various silicones; various silicone copolymers such as acrylic-silicone graft copolymers; various fluoropolymers; 12-hydroxystearic acid and salts thereof; dextrin fatty acid esters such as dextrin palmitate and dextrin myristate; and silicic anhydride, fumed silica (silicic anhydride ultra-fine particles), magnesium aluminum silicate, magnesium sodium silicate, metal soaps, metal dialkyl phosphates, bentonite, hectorite, organo-modified clay mineral, sucrose fatty acid esters, and fructooligosaccharide fatty acid esters. Among them, cellulose and derivatives thereof, alginic acid and salts thereof, polyvinyl alcohol, hyaluronic acid and salts thereof, and collagen are preferable.

Preferable examples of the solvents and the propellants include lower alcohols such as ethanol, 2-propanol (isopropyl alcohol), butanol, and isobutyl alcohol; glycols such as propylene glycol, 1,3-butylene glycol, diethylene glycol, dipropylene glycol, and isopentyldiol; glycol ethers such as diethylene glycol monoethyl ether (ethoxydiglycol), ethylene glycol monoethyl ether, ethylene glycol monobutyl ether, triethylene glycol monoethyl ether, diethylene glycol diethyl ether, diethylene glycol dibutyl ether, propylene glycol monoethyl ether, and dipropylene glycol monoethyl ether; glycol ether esters such as ethylene glycol monoethyl ether acetate, diethylene glycol monoethyl ether acetate, and propylene glycol monoethyl ether acetate; glycol esters such as diethoxyethyl succinate and ethylene glycol disuccinate; benzyl alcohol, benzyloxyethanol, propylene carbonate, dialkyl carbonate, acetone, ethyl acetate, and N-methylpyrrolidone; toluene; fluorocarbon and next-generation fron; and propellants such as LPG, dimethyl ether, and carbon dioxide gas.

Preferable examples of the antioxidants include tocopherol (vitamin E) and tocopherol derivatives such as tocopherol acetate; BHT and BHA; gallic acid derivatives such as propyl gallate; vitamin C (ascorbic acid) and/or derivatives thereof; erythorbic acid and derivatives thereof; sulfites such as sodium sulfite; hydrogen sulfites such as sodium hydrogen sulfite; thiosulfates such as sodium thiosulfate; hydrogen metasulfites; thiotaurine and hypotaurine; and thioglycerol, thiourea, thioglycolic acid, and cysteine hydrochloride.

Preferable examples of the reducing agents include thioglycolic acid, cysteine, and cysteamine.

Preferable examples of the oxidizing agents include a hydrogen peroxide solution, ammonium persulfate, sodium bromate, and percarbonic acid.

Preferable examples of the preservatives, the antimicrobial agents, and the antiseptics include hydroxybenzoic acids and salts and esters thereof such as methylparaben, ethylparaben, propylparaben, and butylparaben; salicylic acid; sodium benzoate; phenoxyethanol; isothiazolinone derivatives such as methylchloroisothiazolinone and methylisothiazolinone; imidazolinium urea; dehydroacetic acid and salts thereof; phenols; halogenated bisphenols such as triclosan, acid amides, and quaternary ammonium salts; trichlorocarbanilide, zinc pyrithione, benzalkonium chloride, benzethonium chloride, sorbic acid, chlorhexidine, chlorhexidine gluconate, halocarban, hexachlorophene, and hinokitiol; phenol and other phenols such as isopropylphenol, cresol, thymol, p-chlorophenol, phenylphenol, and sodium phenylphenolate; and phenylethyl alcohol, photosensitive dyes, antimicrobial zeolite, and a silver ion.

Preferable examples of the chelating agents include edetates (ehylenediamine tetraacetates) such as EDTA, EDTA-2Na, EDTA-3Na, and EDTA-4Na; hydroxyethylethylenediaminetriacetates such as HEDTA-3Na; pentetates (diethylenetriaminepentaacetate); phytic acid; phosphonic acids such as etidronic acid, and salts thereof including sodium salts thereof; sodium oxalate; polyamino acids such as polyaspartic acid and polyglutamic acid; sodium polyphosphate, sodium metaphosphate, and phosphoric acid; and sodium citrate, citric acid, alanine, dihydroxyethylglycine, gluconic acid, ascorbic acid, succinic acid, and tartaric acid.

Preferable examples of the pH-adjusters, acids, and alkalis include citric acid, sodium citrate, lactic acid, sodium lactate, potassium lactate, glycolic acid, succinic acid, acetic acid, sodium acetate, malic acid, tartaric acid, fumaric acid, phosphoric acid, hydrochloric acid, sulfuric acid, monoethanolamine, diethanolamine, triethanolamine, isopropanolamine, triisopropanolamine, 2-amino-2-methyl-1,3-propanediol, 2-amino-2-hydroxymethyl-1,3-propanediol, arginine, sodium hydroxide, potassium hydroxide, an aqueous ammonia solution, guanidine carbonate, and ammonium carbonate.

Preferable examples of the powders include inorganic powders of various sizes and shapes such as mica, talc, kaolin, sericite, montmorillonite, kaolinite, mica, muscovite, phlogopite, synthetic mica, lepidolite, biotite, vermiculite, magnesium carbonate, calcium carbonate, aluminum silicate, barium silicate, calcium silicate, magnesium silicate, strontium silicate, metal tungstates, magnesium zeolite, barium sulfate, calcined calcium sulfate, calcium phosphate, fluorapatite, hydroxyapatite, ceramic powder, bentonite, smectite, clay, mud, metal soaps (zinc myristate, calcium palmitate, and aluminum stearate, for example), calcium carbonate, red iron oxide, yellow iron oxide, black iron oxide, ultramarine, prussian blue, carbon black, titanium oxide, titanium oxide fine particles and titanium oxide ultrafine particles, zinc oxide, zinc oxide fine particles and zinc oxide ultrafine particles, alumina, silica, fumed silica (silicic anhydride ultrafine particles), titanated mica, fish scale guanine, boron nitride, photochromic pigments, synthetic fluorophlogopite, fine-particle composite powders, gold, and aluminum, and these inorganic powders that are treated with a silicone such as hydrogen silicone and cyclic hydrogen silicone or are otherwise treated with various surface-treating agents such as silane coupling agents and titanium coupling agents to hydrophobize or hydrophilize these inorganic powders; and organic powders, surface-treated organic powders, and organic-inorganic composite powders of various sizes and shapes such as starch, cellulose, nylon powder, polyethylene powder, polymethyl methacrylate powder, polystyrene powder, styrene-acrylate copolymer resin powder, polyester powder, benzoguanamine resin powder, polyethylene terephthalate/polymethyl methacrylate-laminated powder, polyethylene terephthalate/aluminum/epoxy-laminated powder, urethane powder, silicone powder, and Teflon (registered trademark) powder.

Preferable examples of the inorganic salts include sodium chloride-containing salts such as common salt, regular salt, rock salt, sea salt, and natural salt; potassium chloride, aluminum chloride, calcium chloride, magnesium chloride, bittern, zinc chloride, and ammonium chloride; sodium sulfate, aluminum sulfate, aluminum potassium sulfate (alum), aluminum ammonium sulfate, barium sulfate, calcium sulfate, potassium sulfate, magnesium sulfate, zinc sulfate, iron sulfate, and copper sulfate; and sodium phosphates such as mono-, di-, and trisodium phosphates, potassium phosphates, calcium phosphates, and magnesium phosphates.

Preferable examples of the ultraviolet absorbers include benzoate-based ultraviolet absorbers such as p-aminobenzoic acid, p-aminobenzoic acid monoglycerin ester, N,N-dipropoxy p-aminobenzoic acid ethyl ester, N,N-diethoxy p-aminobenzoic acid ethyl ester, N,N-dimethyl p-aminobenzoic acid ethyl ester, N,N-dimethyl p-aminobenzoic acid butyl ester, and N,N-dimethyl p-aminobenzoic acid ethyl ester; anthranilate-based ultraviolet absorbers such as homomenthyl-N-acetylanthranilate; salicylate-based ultraviolet absorbers such as salicylic acid and a sodium salt thereof, amyl salicylate, menthyl salicylate, homomenthyl salicylate, octyl salicylate, phenyl salicylate, benzyl salicylate, and p-isopropanolphenyl salicylate; cinnamate-based ultraviolet absorbers such as octyl cinnamate, ethyl-4-isopropyl cinnamate, methyl-2,5-diisopropyl cinnamate, ethyl-2,4-diisopropyl cinnamate, methyl-2,4-diisopropyl cinnamate, propyl-p-methoxy cinnamate, isopropyl-p-methoxy cinnamate, isoamyl-p-methoxy cinnamate, 2-ethylhexyl p-methoxy cinnamate (octyl p-methoxy cinnamate), 2-ethoxyethyl-p-methoxy cinnamate (cinoxate), cyclohexyl-p-methoxy cinnamate, ethyl-α-cyano-β-phenyl cinnamate, 2-ethylhexyl α-cyano-β-phenyl cinnamate (octocrylene), glyceryl mono-2-ethylhexanoyl-di-p-methoxy cinnamate, and ferulic acid and derivatives thereof; benzophenone-based ultraviolet absorbers such as 2,4-dihydroxybenzophenone, 2,2'-dihydroxy-4-methoxybenzophenone, 2,2'-dihydroxy-4,4'-dimethoxybenzophenone, 2,2',4,4'-tetrahydroxybenzophenone, 2-hydroxy-4-methoxybenzophenone (oxybenzone-3), 2-hydroxy-4-methoxy-4'-methylbenzophenone, 2-hydroxy-4-methoxybenzophenone-5-sulfonate, 4-phenylbenzophenone, 2-ethylhexyl-4'-phenyl-benzophenone-2-carboxylate, 2-hydroxy-4-n-octoxybenzophenone, and 4-hydroxy-3-carboxybenzophenone; 3-(4'-methylbenzylidene)-d,l-camphor and 3-benzylidene-d,l-camphor; 2-phenyl-5-methylbenzoxazole; 2,2'-hydroxy-5-methylphenylbenzotriazole; 2-(2'-hydroxy-5'-tert-octylphenyl)benzotriazole; 2-(2'-hydroxy-5'-methylphenylbenzotriazole; dibenzalazines; dianisoylmethane; 5-(3,3-dimethyl-2-norbornylidene)-3-pentan-2-one; dibenzoylmethane derivatives such as 4-tert-butylmethoxydibenzoylmethane; octyl triazone; urocanic acid, and urocanic acid derivatives such as ethyl urocanate; and 2-(2'-hydroxy-5'-methylphenyl)benzotriazole, 1-(3,4-dimethoxyphenyl)-4,4-dimethyl-1,3-pentanedione, hydantoin derivatives such as 2-ethylhexyl dimethoxybenzylidene dioxoimidazolidine propionate, phenylbenzimidazole sulfonic acid, terephthalylidene dicamphor sulfonic acid, drometrizole trisiloxane, methyl anthranilate, rutin and derivatives thereof, and orizanol and derivatives thereof.

Preferable examples of the skin-brightening agents include hydroquinone glycosides such as arbutin and α-arbutin, and esters thereof; ascorbic acid and ascorbic acid derivatives such as ascorbyl phosphate salts including sodium ascorbyl phosphate and magnesium ascorbyl phosphate, ascorbyl fatty acid esters including ascorbyl tetraisopalmitate, ascorbic acid alkyl ethers including ascorbic acid ethyl ether, ascorbic acid glucosides including ascorbic acid 2-glucoside and fatty acid esters thereof, ascorbyl sulfurate, and tocopheryl ascorbyl phosphate; and kojic acid, ellagic acid, tranexamic acid and derivatives thereof, ferulic acid and derivatives thereof, placenta extract, glutathione, orizanol, butyl resorcinol, and plant extracts such as oil-soluble Chamomilla recutita extract, oil-soluble licorice extract, Tamarix chinensis extract, and Saxifraga sarmentosa extract.

Preferable examples of the vitamins and derivatives thereof include the vitamin A group such as retinol, retinol acetate, and retinol palmitate; the vitamin B group such as thiamine hydrochloride, thiamine sulfate, riboflavin, riboflavin acetate, pyridoxine hydrochloride, pyridoxine dioctanoate, pyridoxine dipalmitate, flavin adenine dinucleotide, cyanocobalamine, folic acids, nicotinic acids such as nicotinamide and benzyl nicotinate, and cholines; the vitamin C group such as ascorbic acid and salts thereof including sodium thereof; vitamin D; the vitamin E group such as α-, β-, γ-, and δ-tocopherols; other vitamins such as pantothenic acid and biotin; ascorbic acid derivatives such as ascorbyl phosphate salts including ascorbyl phosphate sodium salt and ascorbyl phosphate magnesium salt, ascorbyl fatty acid esters including ascorbyl tetraisopalmitate, ascorbyl stearate, ascorbyl palmitate, and ascorbyl dipalmitate, ascorbic acid alkyl ethers including ascorbic acid ethyl ether, ascorbic acid glucosides including ascorbic acid 2-glucoside and fatty acid esters thereof, and tocopheryl ascorbyl phosphate; and vitamin derivatives such as tocopherol derivatives including tocopherol nicotinate, tocopherol acetate, tocopherol linoleate, tocopherol ferulate, and tocopherol phosphate, tocotrienol, and other various vitamin derivatives.

Preferable examples of the hair growth-promoting agents, the blood circulation-promoters, and the stimulating agents include plant extracts and tinctures such as Swertia herb extract, Capsicum frutescens tincture, ginger tincture, ginger extract, and cantharides tincture; and capsaicin, nonylic acid vanillylamide, zingerone, ichthammol, tannic acid, borneol, cyclandelate, cinnarizine, tolazoline, acetylcholine, verapamil, cepharanthine, γ-orizanol, vitamin E and derivatives thereof including tocopherol nicotinate and tocopherol acetate, γ-orizanol, nicotinic acid and derivatives thereof including nicotinamide, benzyl nicotinate, inositol hexanicotinate, and nicotinic alcohol, allantoin, Kankoso 301, Kankoso 401, carpronium chloride, pentadecanoic acid monoglyceride, flavanonol derivatives, stigmasterol and stigmastanol and glycosides thereof, and minoxidil.

Preferable examples of the hormones include estradiol, estrone, ethynylestradiol, cortisone, hydrocortisone, and prednisone. Preferable examples of other substances with drug efficacy such as the anti-wrinkle agents, the anti-aging agents, the tightening agents, the cool-feeling agents, the warm-feeling agents, the wound-healing promoters, the abirritants, the analgesics, and the cell activators include retinols, retinoic acids, and tocopheryl retinoate; lactic acid, glycolic acid, gluconic acid, fruit acid, and salicylic acid and derivatives thereof including glycosides thereof and esters thereof, and α- and β-hydroxy acids and derivatives thereof such as hydroxycapric acid, long-chain α-hydroxy fatty acids, long-chain α-hydroxy fatty acid cholesteryl esters; γ-aminobutyric acid and γ-amino-β-hydroxybutyric acid; carnitine; carnosine; creatine; ceramides and sphingosines; caffeine, xanthine, and the like and derivatives thereof; antioxidizing agents and active oxygen scavengers such as coenzyme Q10, carotin, lycopene, astaxanthin, lutein, α-lipoic acid, colloidal platinum nanoparticles, and fullerenes; catechins; flavones such as quercetin; isoflavones; gallic acid and sugar ester derivatives thereof; polyphenols such as tannin, sesamin, proanthocyanidin, chlorogenic acid, and apple polyphenol; rutin and derivatives thereof including glycosides thereof; hesperidin and derivatives thereof including glycosides thereof; lignan glycoside; licorice extract-related substances such as glabridin, glabrene, liquiritin, and isoliquiritin; lactoferrin; shogaol and gingerol; perfume substances such as menthol and cedrol, and derivatives thereof; capsaicin, vanillin, and the like and derivatives thereof; insect repellents such as diethyltoluamide; and complexes of physiologically active substances and cyclodextrins.

Preferable examples of the plant, animal, and microbial extracts include extracts such as iris extract, Angelica keiskei extract, Thujopsis dolabrata extract, asparagus extract, avocado extract, Hydrangea serrata extract, almond extract, Althaea officinalis extract, Arnica montana extract, aloe extract, apricot extract, apricot kernel extract, Gingko biloba extract, Artemisia capillaris flower extract, fennel seed extract, turmeric root extract, oolong tea extract, Arctostaphylos uva-ursi leaf extract, Rosa multiflora fruit extract, Echinacea angustifolia leaf extract, Isodonis japonicus extract, Scutellaria baicalensis extract, Phellodendron amurense bark extract, Coptis japonica root extract, Hordeum vulgare extract, Panax ginseng extract, Hypericum perforatum extract, Lamium album extract, Ononis spinosa extract, Nasturtium officinale extract, orange extract, dried sea water residues, seaweed extract, Persimmon leaf extract, Pyracantha fortuneana extract, hydrolyzed elastin, hydrolyzed wheat powder, hydrolyzed silk, Pueraria lobata root extract, Chamomilla recutita extract, oil-soluble Chamomilla recutita extract, Daucus carota sativa extract, Artemisia capillaris extract, Avena fatua extract, carcade extract, licorice extract, oil-soluble licorice extract, kiwi fruit extract, kiou extract, Auricularia auricula-judae extract, Cinchona succirubra extract, cucumber extract, Paulownia tomentosa leaf extract, guanosine, guava extract, Sophora angustifolia extract, gardenia extract, Sasa veitchii extract, Sophora angustifolia extract, walnut extract, chestnut extract, grapefruit extract, Clematis vitalba extract, black rice extract, black sugar extract, black vinegar, Chlorella vulgaris extract, Morus alba extract, Gentiana lutea extract, Geranium thunbergii extract, black tea extract, yeast extract, magnolia bark extract, coffee seed extract, Arctium lappa root extract, rice extract, fermented rice extract, fermented rice bran extract, rice germ oil, *Symphytum officinale* extract, collagen, *Vaccinium vitis-idaea* extract, *Asarum sieboldi* extract, *Bupleurum falcatum* extract, umbilical extract, saffron extract, *salvia* extract, *Saponaria officinalis* extract, *sasa* extract, *Crataegus cuneata* fruit extract, *Bombyx mori* excrementum extract, *Zanthoxylum piperitum* extract, *Corthellus shiitake* extract, *Rehmannia glutinosa* extract, *Lithospermum erythrorhizon* root extract, *Perilla ocymoides* extract, *Tilia cordata* extract, *Spiraea ulmaria* extract, jatoba extract, *Paeonia albiflora* extract, ginger extract, *Acorus calamus* root extract, *Betula platyphylla japonica* extract, *Tremella fuciformis* extract, *Equisetum arvense* extract, *stevia* extract, stevia fermentation product, *Tamarix chinensis* extract, *Hedera helix* extract, *Crataegus oxyacantha* extract, *Sambucus nigra* extract, *Achillea millefolium* extract, *Mentha piperita* extract, sage extract, *Malva sylvestris* extract, *Cnidium officinale* extract, Swertia herb extract, *Morus alba* root extract, Rheum extract, soybean extract, *Zizyphus jujuba* extract, thyme extract, dandelion extract, lichen extract, *Camellia sinensis* leaf extract, clove extract, *Imperata cylindrica* extract, *Citrus unshiu* peel extract, tea tree oil, *Rubus suavissimus* extract, *Capsicum frutescens* extract, *Angelica acutiloba* extract, *Calendula officinalis* extract, *Prunus persica* kernel extract, *Citrus aurantium amara* peel extract, *Houttuynia cordata* extract, tomato extract, natto extract, carrot extract, garlic extract, *Rosa canina* extract, hibiscus extract, *Ophiopogon japonicus* root extract, *Nelumbo nucifera* extract, parsley extract, birch extract, honey, *Hamamelis virginiana* extract, *Parietaria officinalis* extract, *Isodonis japonicus* extract, bisabolol, *Chamaecyparis obtusa* extract, *Bifidobacterium* extract, *Eriobotrya japonica* extract, *Tussilago farfara* extract, *Petasites japonicus* flower stalk extract, *Poria cocos sclerotium* extract, *Ruscus aculeatus* extract, grape extract, grape seed extract, propolis, *Luffa cylindrica* extract, safflower extract, peppermint extract, *Tilia miqueliana* extract, *Paeonia suffruticosa* root extract, hops extract, *Rosa rugosa* flower extract, *Pinus sylvestris* cone extract, horse chestnut extract, *Lysichiton camtschatcense* extract, *Sapindus mukurossi* peel extract, *Melissa officinalis* extract, *Nemacystus decipiens* extract, peach extract, *Centaurea cyanus* extract, *Eucalyptus globulus* extract, *Saxifraga sarmentosa* extract, *Citrus junos* extract, lily extract, *Coix lacryma-jobi* seed extract, *Artemisia princeps* extract, lavender extract, green tea extract, egg shell membrane extract, apple extract, rooibos tea extract, *Ganoderma lucidum* extract, lettuce extract, lemon extract, forsythia extract, *Astragalus sinicus* extract, rose extract, rosemary extract, *Anthemis nobilis* extract, royal jelly extract, and *Sanguisorba officinalis* root extract.

Examples of the antipruritics include diphenhydramine hydrochloride, chlorpheniramine maleate, camphor, and substance P inhibitors.

Examples of the keratin-exfoliating/dissolving agents include salicylic acid, sulfur, resorcin, selenium sulfide, and pyridoxine.

Examples of the antiperspirants include aluminum chlorohydrate, aluminum chloride, zinc oxide, and zinc p-phenolsulfonate.

Examples of the refrigerants include menthol and methyl salicylate.

Examples of the styptics include citric acid, tartaric acid, lactic acid, aluminum potassium sulfate, and tannic acid.

Examples of the enzymes include superoxide dismutases, catalases, lysozyme chloride, lipases, papain, pancreatin, and proteases.

Preferable examples of the nucleic acids include ribonucleic acid and salts thereof, deoxyribonucleic acid and salts thereof, and adenosine triphosphate disodium.

Preferable examples of the perfumes include synthetic perfumes and natural perfumes such as acetyl cedrene, amylcinnamaldehyde, allylamyl glycolate, β-ionone, Iso E Super, isobutylquinoline, iris oil, irone, indole, ylang-ylang oil, undecanal, undecenal, γ-undecalactone, estragole, eugenol, oakmoss, opoponax resinoid, orange oil, eugenol, aurantiol, galaxolide, carvacrol, L-carvone, camphor, canon, carrot seed oil, clove oil, methyl cinnamate, geraniol, geranyl nitrile, isobornyl acetate, geranyl acetate, dimethylbenzylcarbinyl acetate, styralyl acetate, cedryl acetate, terpinyl acetate, p-t-butylcyclohexyl acetate, vetiveryl acetate, benzyl acetate, linalyl acetate, isopentyl salicylate, benzyl salicylate, sandalwood oil, santalol, cyclamen aldehyde, cyclopentadecanolide, methyl dihydrojasmonate, dihydromyrcenol, jasmine absolute, jasmin lactone, cis-jasmone, citral, citronellol, citronellal, cinnamon bark oil, 1,8-cineole, cinnamaldehyde, styrax resinoid, cedarwood oil, cedrene, cedrol, celery seed oil, thyme oil, damascone, damascenone, thymol, tuberose absolute, decanal, decalactone, terpineol, γ-terpinen, triplal, nerol, nonanal, 2,6-nonadienol, nonalactone, patchouli alcohol, vanilla absolute, vanillin, basil oil, patchouli oil, hydroxycitronellal, α-pinene, piperitone, phenethyl alcohol, phenylacetaldehyde, petitgrain oil, hexylcinnamaldehyde, cis-3-hexenol, Peru balsam, vetiver oil, vetiverol, peppermint oil, pepper oil, heliotropin, bergamot oil, benzyl benzoate, borneol, mil resinoid, musk ketone, methyl nonyl acetaldehyde, γ-methyl ionone, menthol, L-menthol, L-menthone, *Eucalyptus globulus* oil, β-ionone, lime oil, lavender oil, D-limonene, linalool, lyral, lilial, lemon oil, rose absolute, rose oxide, rose oil, rosemary oil, and various essential oils, and various perfume blends.

Preferable examples of the coloring agents, the colorants, the dyes, and the pigments include Japanese cosmetic colors such as Brown No. 201, Black No. 401, Violet No. 201, Violet No. 401, Blue No. 1, Blue No. 2, Blue No. 201, Blue No. 202, Blue No. 203, Blue No. 204, Blue No. 205, Blue No. 403, Blue No. 404, Green No. 201, Green No. 202, Green No. 204, Green No. 205, Green No. 3, Green No. 401, Green No. 402, Red No. 102, Red No. 104-1, Red No. 105-1, Red No. 106, Red No. 2, Red No. 201, Red No. 202, Red No. 203, Red No. 204, Red No. 205, Red No. 206, Red No. 207, Red No. 208, Red No. 213, Red No. 214, Red No. 215, Red No. 218, Red No. 219, Red No. 220, Red No. 221, Red No. 223, Red No. 225, Red No. 226, Red No. 227, Red No. 228, Red No. 230-1, Red No. 230-2, Red No. 231, Red No. 232, Red No. 3, Red No. 401, Red No. 404, Red No. 405, Red No. 501, Red No. 502, Red No. 503, Red No. 504, Red No. 505, Red No. 506, Orange No. 201, Orange No. 203, Orange No. 204, Orange No. 205, Orange No. 206, Orange No. 207, Orange No. 401, Orange No. 402, Orange No. 403, Yellow No. 201, Yellow No. 202-1, Yellow No. 202-2, Yellow No. 203, Yellow No. 204, Yellow No. 205, Yellow No. 4, Yellow No. 401, Yellow No. 402, Yellow No. 403-1, Yellow No. 404, Yellow No. 405, Yellow No. 406, Yellow No. 407, and Yellow No. 5; other acid dyes such as Acid Red No. 14; basic dyes such as Arianor Sienna Brown, Arianor Madder Red, Arianor Steel Blue, and Arianor Straw Yellow; nitro dyes such as FTC Yellow No. 2, HC Yellow No. 5, HC Red No. 3, 4-hydoxypropylamino-3-nitrophenol, N,N'-bis(2-hydroxyethyl)-2-nitro-p-phenylenediamine, HC Blue No. 2, and Basic Blue No. 26; disperse dyes; inorganic white pigments such as titanium dioxide and zinc oxide; inorganic red pigments such as iron oxide (red iron oxide) and iron titanate; inorganic brown pigments such as γ-iron oxide; inorganic yellow pigments such as yellow iron oxide and ochre; inorganic black pigments such as black iron oxide and lower-order titanium oxide; inorganic violet pigments such as mango violet and cobalt violet; inorganic green pigments such as chromium oxide, chromium hydroxide, and cobalt titanium oxide; inorganic blue pigments such as ultramarine and prussian blue; pearl pigments such as titanium oxide-coated mica, titanium oxide-coated bismuth oxychloride, titanium oxide-coated talc, colored titanium oxide-coated mica, bismuth oxychloride, and fish scale guanine; metal powder pigments such as aluminum powder, copper powder, and gold; surface-treated inorganic and metallic powder pigments; organic pigments such as zirconium lake, barium lake, and aluminum lake; surface-treated organic pigments; natural coloring agents and natural dyes such as astaxanthin, anthraquinones including alizarin, anthocyanidine, β-carotin, catenal, capsanthin, chalcone, carthamin, quercetin, crocin, chlorophyll, curcumin, cochineal, naphthoquinones including shikonin, bixin, flavones, betacyanin, henna, hemoglobin, lycopene, riboflavin, and rutin; oxidation dye intermediates and couplers such as p-phenylenediamine, toluene-2,5-diamine, o-, m-, and p-aminophenols, m-phenylenediamine, 5-amino-2-methyl phenol, resorcin, 1-naphthol, 2,6-diaminopyridine, and the like, and salts thereof; autoxidizable dyes such as indoline; and dihydroxyacetone.

Preferable examples of the antiphlogistics and the anti-inflammatory agents include glycyrrhizic acid and derivatives thereof, glycyrrhetinic acid derivatives, salicylic acid derivatives, hinokitiol, guaiazulene, allantoin, indomethacin, ketoprofen, ibuprofen, diclofenac, loxoprofen, celecoxib, infliximab, etanercept, zinc oxide, hydrocortisone acetate, prednisone, diphenhydramine hydrochloride, and chlorpheniramine maleate; and plant extracts such as peach leaf extract and *Artemisia princeps* leaf extract.

Preferable examples of the anti-asthmatic agents, the drugs for chronic obstructive pulmonary disease, the anti-allergic agents, and the immunomodulators include aminophylline, theophyllines, steroids (fluticasone, beclomethasone, and the like), leukotriene antagonists, thromboxane inhibitors, Intal, β2-agonists (formoterol, salmeterol, albuterol, tulobuterol, clenbuterol, epinephrine, and the like), tiotropium, ipratropium, dextromethorphan, dimemorfan, bromhexine, tranilast, ketotifen, azelastine, cetirizine, chlorpheniramine, mequitazine, tacrolimus, cyclosporin, sirolimus, methotrexate, cytokine modulators, interferon, omalizumab, and proteins and antibodies.

Preferable examples of the anti-infective agents and the antifungal agents include oseltamivir, zanamivir, and itraconazole. Other than these, known cosmetic ingredients, known pharmaceutical ingredients, known food ingredients, and the like such as ingredients described in The Japanese Standards of Cosmetic Ingredients, Japanese Cosmetic Ingredients Codex, Japanese Cosmetic Labeling Name list issued by Japan Cosmetic Industry Association, INCI dictionary (The International Cosmetic Ingredient Dictionary and Handbook), Japanese Standards of Quasi-drug Ingredients, Japanese Pharmacopoeia, Japanese Pharmaceutical Excipients, Japan's Specifications and Standards for Food Additives, and the like and ingredients described in Japanese and foreign patent publications and Patent Application Publications (including Japanese Translations of PCT International Applications and Domestic Re-Publications of PCT International Applications) categorized as International Patents Classification IPC of A61K7 and A61K8 can be included in a known combination and in a known formulation ratio or in a known formulation amount.

[Method for Producing Hydrogel]

According to the present invention, a hydrogel can be produced by mixing the disperse phase (A), that is, a disperse phase including the lipid peptide-based gelator, the particular fatty acid salt, and water, and the disperse phase (B) including the water-soluble acidic polymer.

More specifically, the method for producing a hydrogel according to the present invention includes:

a) preparing the disperse phase (A) including the lipid peptide-based gelator, water, and the fatty acid salt, b) adding the disperse phase (B) including the water-soluble acidic polymer to the disperse phase (A), and c) stirring the resulting mixture at room temperature and then leaving the resulting mixture still standing to form a hydrogel.

The step a) of preparing the disperse phase (A) is preferably carried out by mixing the lipid peptide-based gelator, water, and the fatty acid salt at a high temperature with stirring and then leaving the resulting mixture to cool to reach room temperature.

[Hydrogel]

A hydrogel formed from the hydrogel-forming material and the disperse phases and a gel obtained by the method described above are also within the scope of the present invention.

EXAMPLES

The present invention will be described in more detail by examples and test examples. The scope of the present invention, however, is not limited to these examples.

Synthesis Example 1: Synthesis of Lipid Peptide (N-Palmitoyl-Gly-his)

A lipid peptide used in this example as a gelator was synthesized by a method below.

14.2 g (91.6 mmol) of histidine, 30.0 g (91.6 mmol) of N-palmitoyl-Gly-methyl, and 300 g of toluene were added to a 500-mL four-necked flask, to which 35.3 g (183.2 mmol) of a 28% methanol solution of sodium methoxide as a base was added, and the resulting solution was heated in an oil bath to 60° C. and was stirred for 1 hour. Subsequently, the resulting solution that was removed from the oil bath was left to cool to reach 25° C., was reprecipitated with 600 g of acetone, and was filtered. The resulting solid was dissolved in a mixed solution of 600 g of water and 750 g of methanol, to which 30.5 ml (183.2 mmol) of 6-N hydrochloric acid was added for neutralization to precipitate a solid, which was filtered. The resulting solid was then dissolved in a mixed solution of 120 g of tetrahydrofuran and 30 g of water at 60° C., to which 150 g of ethyl acetate was added, and the resulting solution was cooled from 60° C. to 30° C. Subsequently, the precipitated solid was filtrated. The resulting solid was dissolved in a solvent of 120 g of tetrahydrofuran and 60 g of acetonitrile and then heated to 60° C. The resulting solution was stirred for 1 hour and then cooled, followed by filtration. The resulting solid was washed with 120 g of water and filtrated, followed by drying under reduced pressure to obtain 26.9 g (yield: 65%) of a white crystal of a free form of N-palmitoyl-Gly-His (hereinafter, also simply called N-palmitoyl-Gly-His).

Example 1 to Example 14 and Comparative Example 1 to Comparative Example 3: Preparation of Disperse Phase (A) (Premix) Including N-Palmitoyl-Gly-his and Evaluation of Dispersibility Thereof The N-palmitoyl-Gly-His (called Pal-GH in tables) prepared in the synthesis example, sodium palmitate (manufactured by Tokyo Chemical Industry Co., Ltd.) as an additive, and water were placed in a 300-mL beaker at a proportion shown in the following tables, followed by heating to the liquid temperature of 80° C. for 20 minutes to 90 minutes with stirring at 300 rpm. After the heating was terminated, the resulting solution was left to cool for 1 hour with stirring at 300 rpm. The amount of water lost by evaporation was added, followed by stirring at 300 rpm for another 1 minute. The resulting solution was left at room temperature overnight or longer to prepare a disperse phase (A). A LABORATORY HIGH POWER MIXER manufactured by As One Corporation was used as a mixer for stirring.

Dispersibility in preparation of the disperse phase (A) was evaluated by visual observation as, ○ when the N-palmitoyl-Gly-His and the additive were dispersed in water during the heating process and neither separation of water nor deposition of solid matter from the resulting disperse phase (A) occurred, or as x when the N-palmitoyl-Gly-His and/or the additive did not disperse in water during the heating process and solid matter could be observed. The pH of the disperse phase (A) was measured with a twin pH meter (manufactured by As One Corporation).

The results are shown in Table 1 to Table 4.

TABLE 1

| Composition | Examples | | | | Comparative Example |
|---|---|---|---|---|---|
| (% by mass) | 1 | 2 | 3 | 4 | 1 |
| Pal-GH | 1.0 | 1.0 | 1.0 | 1.0 | 1.0 |
| Sodium palmitate*1 | 0.30 | 0.61 | 1.23 | 1.85 | — |
| Water | Rest | Rest | Rest | Rest | Rest |
| Total | 100 | 100 | 100 | 100 | 100 |
| Test results are as follows | | | | | |
| Dispersibility in disperse phase (A) | ○ | ○ | ○ | ○ | X |
| pH | 10.3 | 10.3 | 9.7 | 10.3 | — |

*1 manufactured by Tokyo Chemical Industry Co., Ltd.

TABLE 2

| Composition | Examples | | | | |
|---|---|---|---|---|---|
| (% by mass) | 5 | 6 | 7 | 8 | 9 |
| Pal-GH | 0.8 | 0.8 | 0.8 | 0.6 | 0.6 |
| Sodium palmitate*1 | 0.25 | 0.49 | 1.48 | 0.18 | 0.37 |
| Water | Rest | Rest | Rest | Rest | Rest |
| Total | 100 | 100 | 100 | 100 | 100 |
| Test results are as follows | | | | | |
| Dispersibility in disperse phase (A) | ○ | ○ | ○ | ○ | ○ |
| pH | 10.3 | 10.3 | 10.2 | 10.4 | 10.4 |

*1 manufactured by Tokyo Chemical Industry Co., Ltd.

TABLE 3

| Composition | Examples | | | | |
|---|---|---|---|---|---|
| (% by mass) | 10 | 11 | 12 | 13 | 14 |
| Pal-GH | 0.6 | 0.5 | 0.5 | 0.4 | 0.4 |
| Sodium palmitate*1 | 1.11 | 0.15 | 0.30 | 0.24 | 0.2 |
| Water | Rest | Rest | Rest | Rest | Rest |
| Total | 100 | 100 | 100 | 100 | 100 |
| Test results are as follows | | | | | |
| Dispersibility in disperse phase (A) | ○ | ○ | ○ | ○ | ○ |
| pH | 10.3 | 10.3 | 10.4 | 10.4 | 10.3 |

*1 manufactured by Tokyo Chemical Industry Co., Ltd.

TABLE 4

| Composition | Comparative Examples | |
|---|---|---|
| (% by mass) | 2 | 3 |
| Pal-GH | 0.4 | — |
| Sodium palmitate*1 | — | 0.2 |
| Water | Rest | Rest |
| Total | 100 | 100 |
| Test results are as follows | | |
| Dispersibility in disperse phase (A) | X | X |
| pH | 7.8 | 10.5 |

*1 manufactured by Tokyo Chemical Industry Co., Ltd.

Example 15 to Example 52 and Comparative Example 4 and Comparative Example 5: Test for Neutralization and Gelation of Disperse Phase (A) (Premix) Including N-palmitoyl-Gly-His The disperse phase (A) including the N-palmitoyl-Gly-His obtained in Example 1 to Example 14 was placed in a 200-mL beaker at a proportion shown in the following tables, and, while stirring at 300 rpm, a disperse phase (B) (a polyacrylic acid (PAA) dispersion or a carbomer dispersion) shown below was added thereto, followed by stirring at 300 rpm for 1 minute to prepare a hydrogel-forming material. A LABORATORY HIGH POWER MIXER manufactured by As One Corporation was used for stirring. The resulting mixture was left at room temperature for 1 hour and then a portion thereof was placed in a Mighty Vial (No. 3, manufactured by Maruemu Corporation).

Hydrogelation ability was evaluated as "gelled (○)" when inversion of the vial did not make the solution flow down because the solution had lost its fluidity or as "not gelled (x)" when the solution flowed down. Occurrence of syneresis in gel was also observed. In the case where the mixture was gelled, the pH of the gel was measured with a twin pH meter (manufactured by As One Corporation), while in the case where the mixture was not gelled, the pH of the liquid was measured in the same manner. Final compositions after the hydrogelation test and the test results are shown in the following tables. In the tables, the symbol "-" refers to the case where no test was performed.

TABLE 5

| Composition (% by mass) | | Examples | | | |
|---|---|---|---|---|---|
| | | 15 | 16 | 17 | 18 |
| Disperse phase | Example 1 | 50 | | | |
| | Example 2 | | 50 | | |
| | Example 3 | | | 50 | |
| | Example 4 | | | | 50 |
| 0.4% PAA*2 dispersion | | 50 | 50 | 50 | 50 |
| Water | | | | | |
| Total | | 100 | 100 | 100 | 100 |
| Pal-GH | | 0.5 | 0.5 | 0.5 | 0.5 |
| Sodium palmitate | | 0.15 | 0.305 | 0.615 | 0.925 |
| PAA*2 | | 0.2 | 0.2 | 0.2 | 0.2 |
| Water | | Rest | Rest | Rest | Rest |
| Total | | 100 | 100 | 100 | 100 |
| Test Results | | | | | |
| Evaluation of hydrogelation ability | | ○ | ○ | ○ | ○ |
| pH | | 5.3 | 6.2 | 7.5 | 8.5 |

*2 polyacrylic acid (molecular weight: 1,000,000) manufactured by Wako Pure Chemical Industries, Ltd.

TABLE 6

| Composition (% by mass) | | Examples | | | | |
|---|---|---|---|---|---|---|
| | | 19 | 20 | 21 | 22 | 23 |
| Disperse phase | Example 2 | 50 | | | 50 | 50 |
| | Example 3 | | 50 | 50 | | |
| 1.0% PAA*2 dispersion | | | | 50 | | |
| 0.4% PAA*2 dispersion | | | | | 50 | |
| 0.2% PAA*2 dispersion | | 50 | | | | |
| 0.4% PAA*3 dispersion | | | | | 50 | |
| 0.4% PAA*4 dispersion | | | | | | 50 |
| Water | | | | | | |
| Total | | 100 | 100 | 100 | 100 | 100 |
| Pal-GH | | 0.5 | 0.5 | 0.5 | 0.5 | 0.5 |
| Sodium palmitate | | 0.305 | 0.615 | 0.615 | 0.305 | 0.305 |
| PAA*2 | | 0.1 | 0.5 | 0.2 | | |
| PAA*3 | | | | | 0.2 | |
| PAA*4 | | | | | | 0.2 |
| Water | | Rest | Rest | Rest | Rest | Rest |
| Total | | 100 | 100 | 100 | 100 | 100 |

TABLE 6-continued

| Composition (% by mass) | Examples | | | | |
|---|---|---|---|---|---|
| | 19 | 20 | 21 | 22 | 23 |
| Test Results | | | | | |
| Evaluation of hydrogelation ability | ○ | ○ | ○ | X | X |
| pH | 8.8 | 5.3 | 7.1 | 6.0 | 6.1 |

*2 polyacrylic acid (molecular weight: 1,000,000) manufactured by Wako Pure Chemical Industries, Ltd.
*3 polyacrylic acid (molecular weight: 25,000) manufactured by Wako Pure Chemical Industries, Ltd.
*4 polyacrylic acid (molecular weight: 5,000) manufactured by Wako Pure Chemical Industries, Ltd.

TABLE 7

| Composition (% by mass) | | Examples | | | |
|---|---|---|---|---|---|
| | | 24 | 25 | 26 | 27 |
| Disperse phase | Example 2 | 25 | | | |
| | Example 5 | | 50 | | |
| | Example 6 | | | 50 | |
| | Example 7 | | | | 50 |
| 0.4% PAA*2 dispersion | | | | 50 | |
| 0.32% PAA*2 dispersion | | | 50 | | 50 |
| 0.2% PAA*2 dispersion | | 50 | | | |
| Water | | 25 | | 25 | |
| Total | | 100 | 100 | 100 | 100 |
| Pal-GH | | 0.25 | 0.4 | 0.4 | 0.4 |
| Sodium palmitate | | 0.152 | 0.109 | 0.245 | 0.741 |
| PAA*2 | | 0.1 | 0.16 | 0.2 | 0.16 |
| Water | | Rest | Rest | Rest | Rest |
| Total | | 100 | 100 | 100 | 100 |
| Test Results | | | | | |
| Evaluation of hydrogelation ability | | X | ○ | ○ | X |
| pH | | 6.6 | 5.3 | 6.2 | 9.1 |

*2 polyacrylic acid (molecular weight: 1,000,000) manufactured by Wako Pure Chemical Industries, Ltd.

TABLE 8

| Composition (% by mass) | | Examples | | | | |
|---|---|---|---|---|---|---|
| | | 28 | 29 | 30 | 31 | 32 |
| Disperse phase | Example 6 | 25 | 12.5 | | | |
| | Example 8 | | | 50 | | |
| | Example 9 | | | | 50 | |
| | Example 10 | | | | | 50 |
| 0.24% PAA*2 dispersion | | | | 50 | 50 | 50 |
| 0.16% PAA*2 dispersion | | 50 | | | | |
| 0.08% PAA*2 dispersion | | | 50 | | | |
| Water | | 25 | 37.5 | | | |
| Total | | 100 | 100 | 100 | 100 | 100 |
| Pal-GH | | 0.2 | 0.1 | 0.3 | 0.3 | 0.3 |
| Sodium palmitate | | 0.123 | 0.061 | 0.09 | 0.185 | 0.555 |
| PAA*2 | | 0.08 | 0.04 | 0.12 | 0.12 | 0.12 |
| Water | | | Rest | Rest | Rest | Rest |
| Total | | 100 | 100 | 100 | 100 | 100 |
| Test Results | | | | | | |
| Evaluation of hydrogelation ability | | X | X | X | ○ | X |
| pH | | 6.4 | 6.8 | 5.5 | 6.4 | 5.3 |

*2 polyacrylic acid (molecular weight: 1,000,000) manufactured by Wako Pure Chemical Industries, Ltd.

TABLE 9

| Composition (% by mass) | Examples | | |
|---|---|---|---|
| | 33 | 34 | 35 |
| Disperse phase  Example 2 | 50 | 50 | 50 |
| 0.2% carbomer*5 dispersion | 50 | | |
| 0.1% carbomer*5 dispersion | | 50 | |
| 0.05% carbomer*5 dispersion | | | 50 |
| Water | | | |
| Total | 100 | 100 | 100 |
| Pal-GH | 0.5 | 0.5 | 0.5 |
| Sodium palmitate | 0.305 | 0.305 | 0.305 |
| Carbomer*5 | 0.1 | 0.05 | 0.025 |
| Water | Rest | Rest | Rest |
| Total | 100 | 100 | 100 |
| Test Results | | | |
| Evaluation of hydrogelation ability | ○ | X | X |
| pH | 7.5 | 9.5 | 9.8 |

*5 Carbopol 940 manufactured by ITO Inc.

TABLE 10

| Composition (% by mass) | Examples | | | |
|---|---|---|---|---|
| | 36 | 37 | 38 | 39 |
| Disperse phase  Example 11 | 50 | | | |
| Example 12 | | 50 | 50 | 50 |
| 0.2% carbomer*5 dispersion | 50 | 50 | | |
| 0.1% carbomer*5 dispersion | | | 50 | |
| 0.05% carbomer*5 dispersion | | | | 50 |
| Water | | | | |
| Total | 100 | 100 | 100 | 100 |
| Pal-GH | 0.25 | 0.25 | 0.25 | 0.25 |
| Sodium palmitate | 0.075 | 0.15 | 0.15 | 0.15 |
| Carbomer*5 | 0.1 | 0.1 | 0.05 | 0.025 |
| Water | Rest | Rest | Rest | Rest |
| Total | 100 | 100 | 100 | 100 |
| Test Results | | | | |
| Evaluation of hydrogelation ability | ○ | ○ | X | X |
| pH | 6.9 | 6.8 | 8.2 | 9.6 |

*5 Carbopol 940 manufactured by ITO Inc.

TABLE 11

| Composition (% by mass) | Examples | | | |
|---|---|---|---|---|
| | 40 | 41 | 42 | 43 |
| Disperse phase  Example 13 | 50 | 50 | | |
| Example 14 | | | 50 | 50 |
| 0.2% carbomer*5 dispersion | 50 | | 50 | |
| 0.1% carbomer*5 dispersion | | 50 | | 50 |
| Water | | | | |
| Total | 100 | 100 | 100 | 100 |
| Pal-GH | 0.2 | 0.2 | 0.2 | 0.2 |
| Sodium palmitate | 0.12 | 0.12 | 0.1 | 0.1 |

TABLE 11-continued

| Composition (% by mass) | Examples | | | |
|---|---|---|---|---|
| | 40 | 41 | 42 | 43 |
| Carbomer*5 | 0.1 | 0.05 | 0.1 | 0.05 |
| Water | Rest | Rest | Rest | Rest |
| Total | 100 | 100 | 100 | 100 |
| Test Results | | | | |
| Evaluation of hydrogelation ability | ○ | X | ○ | X |
| pH | 6.2 | 7.6 | 5.7 | 5.8 |

*5 Carbopol 940 manufactured by ITO Inc.

TABLE 12

| Composition (% by mass) | Examples | | | | |
|---|---|---|---|---|---|
| | 44 | 45 | 46 | 47 | 48 |
| Disperse phase  Example 14 | 25 | 25 | | | |
| Example 2 | | | 50 | 50 | 50 |
| 0.2% carbomer*5 dispersion | 50 | | | | |
| 0.1% carbomer*5 dispersion | | 50 | | | |
| 0.2% carbomer*6 dispersion | | | 50 | | |
| 0.1% carbomer*6 dispersion | | | | 50 | |
| 0.05% carbomer*6 dispersion | | | | | 50 |
| Water | 25 | 25 | | | |
| Total | 100 | 100 | 100 | 100 | 100 |
| Pal-GH | 0.1 | 0.1 | 0.5 | 0.5 | 0.5 |
| Sodium palmitate | 0.05 | 0.05 | 0.305 | 0.305 | 0.305 |
| Carbomer*5 | 0.1 | 0.05 | | | |
| Carbomer*6 | | | 0.1 | 0.05 | 0.025 |
| Water | Rest | Rest | Rest | Rest | Rest |
| Total | 100 | 100 | 100 | 100 | 100 |
| Test Results | | | | | |
| Evaluation of hydrogelation ability | X | X | ○ | X | X |
| pH | 6.3 | 6.6 | 7.9 | 9.3 | 10 |

*5 Carbopol 940 manufactured by ITO Inc.
*6 Hiviswako 105 manufactured by Wako Pure Chemical Industries, Ltd.

TABLE 13

| Composition (% by mass) | Examples | | | |
|---|---|---|---|---|
| | 49 | 50 | 51 | 52 |
| Disperse phase  Example 12 | 50 | 50 | 50 | |
| Example 14 | | | | 50 |
| 0.2% carbomer*6 dispersion | 50 | | | 50 |
| 0.1% carbomer*6 dispersion | | 50 | | |
| 0.05% carbomer*6 dispersion | | | 50 | |
| Water | | | | |
| Total | 100 | 100 | 100 | 100 |
| Pal-GH | 0.25 | 0.25 | 0.25 | 0.2 |
| Sodium palmitate | 0.15 | 0.15 | 0.15 | 0.1 |

TABLE 13-continued

| Composition | Examples | | | |
|---|---|---|---|---|
| (% by mass) | 49 | 50 | 51 | 52 |
| Carbomer*6 | 0.1 | 0.05 | 0.025 | 0.1 |
| Water | Rest | Rest | Rest | Rest |
| Total | 100 | 100 | 100 | 100 |
| Test Results | | | | |
| Evaluation of hydrogelation ability | ○ | X | X | ○ |
| pH | 6.4 | 8.0 | 9.5 | 6.0 |

*6Hiviswako 105 manufactured by Wako Pure Chemical Industries, Ltd.

TABLE 14

| Composition (% by mass) | | Comparative Examples | |
|---|---|---|---|
| | | 4 | 5 |
| Disperse phase | Comparative Example 2 | 50 | |
| | Comparative Example 3 | | 50 |
| | 0.2% carbomer*5 dispersion Water | 50 | 50 |
| Total | | 100 | 100 |
| Pal-GH | | 0.2 | |
| Sodium palmitate | | | 0.1 |
| Carbomer*5 | | 0.1 | 0.1 |
| Water | | Rest | Rest |
| Total | | 100 | 100 |
| Test Results | | | |
| Evaluation of hydrogelation ability | | X | X |
| pH | | 3.7 | 5.9 |

*5Carbopol 940 manufactured by ITO Inc.

Example 53: Gel Spray Test on N-Palmitoyl-Gly-his Hydrogel

The hydrogel-forming material prepared in the examples was placed in a spray vial (Maruemu Corporation, 3 L), followed by spraying two consecutive times toward the center of a glass plate (10 cm×7.5 cm) that was placed 5 cm away from the tip of the nozzle of the spray vial. Observation was performed until the dripping stopped, followed by measurement of the longer diameter and the shorter diameter of the sprayed mark on the glass and the length of the dripping. The results of the spray test are shown in the following tables. In the tables, the symbol "-" refers to the case where no test was performed.

TABLE 15

| | Hydrogel-forming material Nos. (Example Nos.) | | | | | | | |
|---|---|---|---|---|---|---|---|---|
| Test Results | 15 | 16 | 17 | 18 | 19 | 20 | 21 | 22 |
| Spray length (mm) | 14 | 13 | 0 | 13 | 30 | 10 | 0 | — |
| Spray width (mm) | 12 | 17 | 0 | 20 | 32 | 7 | 0 | — |
| Dripping(mm) | 0 | 0 | 0 | 0 | 0 | 0 | 0 | — |

TABLE 16

| | Hydrogel-forming material Nos. (Example Nos.) | | | | | | | | |
|---|---|---|---|---|---|---|---|---|---|
| Test Results | 23 | 24 | 25 | 26 | 27 | 28 | 29 | 30 | 31 |
| Spray length (mm) | — | 25 | 25 | 10 | 26 | 40 | 34 | 24 | 22 |
| Spray width (mm) | — | 30 | 20 | 14 | 24 | 32 | 35 | 31 | 30 |
| Dripping(mm) | — | 0 | 0 | 0 | >20 | 0 | 0 | 10 | 0 |

TABLE 17

| | Hydrogel-forming material Nos. (Example Nos.) | | | | | | |
|---|---|---|---|---|---|---|---|
| Test Results | 32 | 33 | 34 | 35 | 36 | 37 | 38 |
| Spray length (mm) | 28 | 0 | 20 | 10 | 27 | 12 | 35 |
| Spray width (mm) | 30 | 0 | 25 | 7 | 30 | 11 | 30 |
| Dripping(mm) | >20 | 0 | 0 | 0 | 0 | 0 | 0 |

TABLE 18

| | Hydrogel-forming material Nos. (Example Nos.) | | | | | | |
|---|---|---|---|---|---|---|---|
| Test Results | 39 | 40 | 41 | 42 | 43 | 44 | 45 |
| Spray length (mm) | 20 | 20 | 50 | 37 | 40 | 28 | 30 |
| Spray width (mm) | 23 | 23 | 50 | 39 | 35 | 27 | 32 |
| Dripping(mm) | >15 | 0 | 0 | 0 | 0 | 0 | 3 |

TABLE 19

| | Hydrogel-forming material Nos. (Example Nos.) | | | | | | |
|---|---|---|---|---|---|---|---|
| Test Results | 46 | 47 | 48 | 49 | 50 | 51 | 52 |
| Spray length (mm) | 21 | 25 | 24 | 14 | 41 | 38 | 28 |
| Spray width (mm) | 21 | 23 | 25 | 19 | 35 | 34 | 21 |
| Dripping(mm) | 0 | 0 | >15 | 0 | 0 | 5 | 0 |

Example 54: Test to Evaluate Re-Forming Ability of N-Palmitoyl-Gly-his Hydrogel

In a Mighty Vial (No. 3, manufactured by Maruemu Corporation), 4 g of the hydrogel-forming material prepared in the examples was placed, followed by stirring with a vortex mixer (Scientific Industries, Inc.) for 1 minute. Then, the vial was left still standing at room temperature overnight or longer. Evaluation was conducted as "not converted into a sol (Δ)" when no solation was confirmed after mixing with the vortex mixer, as "re-formed (○)" when the solution lost its fluidity after being converted into a sol and left still standing, and inversion of the vial did not make the solution flow down, or as "not re-formed (x)" when the solution flowed down. The symbol "-" refers to the case where no test was performed.

TABLE 20

| | Hydrogel-forming material Nos. (Example Nos.) | | | | | | | |
|---|---|---|---|---|---|---|---|---|
| Test Result | 15 | 16 | 17 | 18 | 19 | 20 | 21 | 22 |
| Hydrogel re-forming ability | ○ | ○ | Δ | X | ○ | Δ | Δ | — |

TABLE 21

| Test Result | Hydrogel-forming material Nos. (Example Nos.) | | | | | | | | |
|---|---|---|---|---|---|---|---|---|---|
| | 23 | 24 | 25 | 26 | 27 | 28 | 29 | 30 | 31 |
| Hydrogel re-forming ability | — | — | X | ○ | — | — | — | — | ○ |

TABLE 22

| Test Result | Hydrogel-forming material Nos. (Example Nos.) | | | | | | |
|---|---|---|---|---|---|---|---|
| | 32 | 33 | 34 | 35 | 36 | 37 | 38 |
| Hydrogel re-forming ability | — | Δ | — | — | ○ | Δ | — |

TABLE 23

| Test Result | Hydrogel-forming material Nos. (Example Nos.) | | | | | | |
|---|---|---|---|---|---|---|---|
| | 39 | 40 | 41 | 42 | 43 | 44 | 45 |
| Hydrogel re-forming ability | — | Δ | — | Δ | — | — | — |

TABLE 24

| Test Result | Hydrogel-forming material Nos. (Example Nos.) | | | | | | |
|---|---|---|---|---|---|---|---|
| | 46 | 47 | 48 | 49 | 50 | 51 | 52 |
| Hydrogel re-forming ability | Δ | — | — | Δ | — | — | — |

Example 55 to Example 73: Test for Neutralization and Gelation of N-Palmitoyl-Gly-his <Preparation of Phase A (Disperse Phase Including Pal-GH)>

The N-palmitoyl-Gly-His prepared in the synthesis example, a fatty acid, a 1-N aqueous sodium hydroxide solution, purified water, and other additives were placed in a 300-mL beaker at a proportion shown in the following tables, followed by heating to a the liquid temperature of 80° C. for 30 minutes with stirring at 300 rpm. The "Rest" in the row "Purified water" refers to the value obtained by subtracting the amount of the components in the phase A and the phase B other than purified water from the sum (100% by mass) of the components in the phase A and the phase B. Then, heating was terminated and the resulting mixture was left to cool for 1 hour with stirring at 300 rpm. The amount of water lost by evaporation was added, followed by stirring at 300 rpm for another 1 minute. The resulting mixture was left at room temperature overnight or longer to prepare a disperse phase including PalGH to serve as a phase A. In Comparative Example 6 to Comparative Example 9, the phases A did not include Pal-GH.

In these examples, A LABORATORY HIGH POWER MIXER manufactured by As One Corporation was used for stirring.

<Preparation of Phase B (Disperse Phase Including Water-Soluble Acidic Polymer)>

A water-soluble acidic polymer (a carboxyvinyl polymer, an acrylic acid-alkyl methacrylate copolymer), purified water, and other additives were placed in a 200-mL beaker at a proportion shown in the following tables, followed by stirring at 300 rpm at room temperature (about 25° C.) to adequately disperse the components to prepare a disperse phase including a water-soluble acidic polymer to serve as a phase B. In Comparative Example 10 and Comparative Example 11, citric acid or lactic acid was used instead of the acidic polymer.

<Preparation of Hydrogel-Forming Material and Hydrogel>

The phase B (disperse phase including a water-soluble acidic polymer) was added to the phase A (disperse phase including PalGH) obtained as described above at room temperature (about 25° C.) with stirring at 300 rpm, followed by stirring for about 10 minutes to prepare a hydrogel-forming material. A portion of the resulting mixture was placed in a Mighty Vial (No. 3, manufactured by Maruemu Corporation), which was then left still standing at room temperature for 1 hour. Hydrogelation ability was evaluated as "hard gel formed (⊙)" when inversion of the vial did not make the solution flow down because the solution had lost its fluidity and the gel formed was hard enough not to disintegrate due to vibration applied thereto, as "gelled (○)" when the gel formed became fluid due to vibration applied thereto, or as "not gelled (x)" when the resulting solution flowed down. A twin pH meter (manufactured by As One Corporation) was used to measure the pH of the gel in the case where the mixture was gelled or the pH of the sol in the case where the mixture was not gelled. Final compositions after the hydrogelation test and the test results are shown in the following tables.

TABLE 25

| Composition (% by mass) | | Examples | | | |
|---|---|---|---|---|---|
| | | 55 | 56 | 57 | 58 |
| A | Pal-GH | 0.5 | 0.5 | 0.2 | 0.2 |
| | palmitic acid*7 | 0.25 | 0.25 | 0.1 | 0.1 |
| | 1 mol/L aqueous sodium hydroxide solution*8 | 1.02 | 1.02 | 0.41 | 0.41 |
| | purified water | Rest | Rest | Rest | Rest |
| B | carboxyvinyl polymer*9 | 0.2 | 0.1 | 0.2 | 0.1 |
| | purified water | 49.8 | 49.9 | 49.8 | 49.9 |
| | Total | 100 | 100 | 100 | 100 |
| | Evaluation of hydrogelation ability | ⊙ | ⊙ | ⊙ | ○ |
| | pH | 6.5 | 8.5 | 5.3 | 6.5 |

*7 manufactured by Kao Corporation. Lunac P-95
*8 manufactured by Junsei Chemical Co., Ltd.
*9 manufactured by ITO Inc. Carbopol 940

TABLE 26

| Composition (% by mass) | | Comparative Examples | | | |
|---|---|---|---|---|---|
| | | 6 | 7 | 8 | 9 |
| A | Pal-GH | 0 | 0 | 0 | 0 |
| | palmitic acid*7 | 0.25 | 0.25 | 0.1 | 0.1 |
| | 1 mol/L aqueous sodium hydroxide solution*8 | 1.02 | 1.02 | 0.41 | 0.41 |

TABLE 26-continued

| Composition (% by mass) | | Comparative Examples | | | |
|---|---|---|---|---|---|
| | | 6 | 7 | 8 | 9 |
| | purified water | Rest | Rest | Rest | Rest |
| B | carboxyvinyl polymer*9 | 0.2 | 0.1 | 0.2 | 0.1 |
| | purified water | 49.8 | 49.9 | 49.8 | 49.9 |
| | Total | 100 | 100 | 100 | 100 |
| | Evaluation of hydrogelation ability | X | X | X | X |
| | pH | 6.8 | 8.2 | 5.5 | 6.5 |

*7 manufactured by Kao Corporation. Lunac P-95
*8 manufactured by Junsei Chemical Co., Ltd.
*9 manufactured by ITO Inc. Carbopol 940

TABLE 27

| Composition (% by mass) | | Examples | | | |
|---|---|---|---|---|---|
| | | 59 | 60 | 61 | 62 |
| A | Pal-GH | 0.5 | 0.5 | 0.2 | 0.2 |
| | stearic acid*10 | 0.25 | 0.25 | 0.1 | 0.1 |
| | oleic acid*11 | — | — | — | — |
| | 1 mol/L aqueous sodium hydroxide solution*8 | 0.92 | 0.92 | 0.37 | 0.37 |
| | purified water | Rest | Rest | Rest | Rest |
| B | carboxyvinyl polymer*9 | 0.2 | 0.1 | 0.2 | 0.1 |
| | purified water | 49.8 | 49.9 | 49.8 | 49.9 |
| | Total | 100 | 100 | 100 | 100 |
| | Evaluation of hydrogelation ability | ⊙ | ⊙ | ⊙ | ○ |
| | pH | 6.5 | 8.2 | 5.3 | 6.3 |

*8 manufactured by Junsei Chemical Co., Ltd.
*9 manufactured by ITO Inc. Carbopol 940
*10 manufactured by Kao Corporation. Lunac S-98
*11 manufactured by Kao Corporation. Lunac O-LL-V

TABLE 28

| Composition (% by mass) | | Examples | | | |
|---|---|---|---|---|---|
| | | 63 | 64 | 65 | 66 |
| A | Pal-GH | 0.5 | 0.5 | 0.2 | 0.2 |
| | stearic acid*10 | — | — | — | — |
| | oleic acid*11 | 0.25 | 0.25 | 0.1 | 0.1 |
| | 1 mol/L aqueous sodium hydroxide solution*8 | 0.92 | 0.92 | 0.37 | 0.37 |
| | purified water | Rest | Rest | Rest | Rest |
| B | carboxyvinyl polymer*9 | 0.2 | 0.1 | 0.2 | 0.1 |
| | purified water | 49.8 | 49.9 | 49.8 | 49.9 |
| | Total | 100 | 100 | 100 | 100 |
| | Evaluation of hydrogelation ability | ⊙ | ⊙ | ⊙ | ○ |
| | pH | 6.5 | 7.8 | 5.6 | 5.7 |

*8 manufactured by Junsei Chemical Co., Ltd.
*9 manufactured by ITO Inc. Carbopol 940
*10 manufactured by Kao Corporation. Lunac S 98
*11 manufactured by Kao Corporation. Lunac O-LL-V

TABLE 29

| Composition (% by mass) | | Examples | | | | |
|---|---|---|---|---|---|---|
| | | 67 | 68 | 69 | 70 | 71 |
| A | Pal-GH | 0.5 | 0.5 | 0.5 | 0.5 | 0.5 |
| | palmitic acid*7 | 0.25 | 0.25 | 0.25 | 0.25 | 0.25 |
| | 1 mol/L aqueous sodium hydroxide solution*8 | 1.02 | 1.02 | 1.02 | 1.02 | 1.02 |
| | 1,3-butylene glycol*12 | | 10 | | | |
| | glycerin*13 | | | 10 | | |
| | purified water | Rest | Rest | Rest | Rest | Rest |
| B | carboxyvinyl polymer*9 | 0.2 | 0.2 | 0.2 | 0.2 | 0.2 |
| | 1,3-butylene glycol*12 | | | | 10 | |
| | Glycerin*13 | | | | | 10 |
| | purified water | 49.8 | 49.8 | 49.8 | 39.8 | 39.8 |
| | Total | 100 | 100 | 100 | 100 | 100 |
| | Evaluation of hydrogelation ability | ⊙ | ⊙ | ⊙ | ⊙ | ⊙ |
| | pH | 6.5 | 6.6 | 6.7 | 6.8 | 6.7 |

*7 manufactured by Kao Corporation. Lunac P-95
*8 manufactured by Junsei Chemical Co., Ltd.
*9 manufactured by ITO Inc. Carbopol 940
*12 manufactured by ITO Inc.
*13 manufactured by ITO Inc.

TABLE 30

| Composition (% by mass) | | Examples | | Comparative Examples | |
|---|---|---|---|---|---|
| | | 72 | 73 | 10 | 11 |
| A | Pal-GH | 0.5 | 0.5 | 0.5 | 0.5 |
| | palmitic acid*7 | 0.25 | 0.25 | 0.25 | 0.25 |
| | 1 mol/L aqueous sodium hydroxide solution*8 | 1.02 | 1.02 | 1.02 | 1.02 |
| | purified water | Rest | Rest | Rest | Rest |
| B | carboxyvinyl polymer*9 | 0.2 | | | |
| | acrylic acid-alkyl methacrylate copolymer*14 | | 0.2 | | |

TABLE 30-continued

| Composition (% by mass) | Examples | | Comparative Examples | |
|---|---|---|---|---|
| | 72 | 73 | 10 | 11 |
| citric acid*15 | | | 0.2 | |
| lactic acid*16 | | | | 0.2 |
| purified water | 49.8 | 49.8 | 49.8 | 49.8 |
| Total | 100 | 100 | 100 | 100 |
| Evaluation of hydrogelation ability | ⊙ | ⊙ | X | X |
| pH | 6.5 | 6.5 | 4.2 | 4.3 |

*7 manufactured by Kao Corporation. Lunac P-95
*8 manufactured by Junsei Chemical Co., Ltd.
*9 manufactured by ITO Inc. Carbopol 940
*14 manufactured by Nikko Chemicals Co., Ltd. PEMULEN TR-1
*15 manufactured by Wako Pure Chemical Industries, Ltd.
*16 manufactured by Wako Pure Chemical Industries, Ltd.

The invention claimed is:

1. A hydrogel-forming material comprising:
   (i) a disperse phase (A) including 0.2 to 0.5% by mass, relative to a total mass of a formed hydrogel, of a lipid peptide-based gelator consisting of a compound of Formula (1) or a pharmaceutically usable salt thereof, water, and 0.1 to 0.25% by mass, relative to the total mass of the formed hydrogel, of a fatty acid salt, and a disperse phase (B) that includes 0.1 to 0.2% by mass, relative to the total mass of the formed hydrogel, of a carboxyvinyl polymer increasing viscosity by neutralization; or
   (ii) a disperse phase (A) including 0.3 to 0.5% by mass, relative to a total mass of a formed hydrogel, of a lipid peptide-based gelator consisting of a compound of Formula (1) or a pharmaceutically usable salt thereof, water, and 0.1 to 0.305% by mass, relative to the total mass of the formed hydrogel, of a fatty acid salt, and a disperse phase (B) that includes 0.2% by mass, relative to the total mass of the formed hydrogel, of an acrylic acid-alkyl methacrylate copolymer increasing viscosity by neutralization, or 0.1 to 0.5% by mass, relative to the total mass of the formed hydrogel, of a polyacrylic acid increasing viscosity by neutralization:

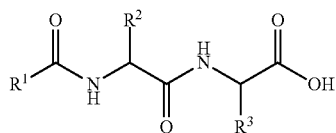
(1)

where $R^1$ is a $C_{9-23}$ aliphatic group, $R^2$ is a hydrogen atom or a $C_{1-4}$ alkyl group that optionally has a $C_{1-2}$ branched chain, $R^3$ is a —$(CH_2)_n$—X group, n is a number of 1 to 4, X is an amino group, a guanidino group, a —$CONH_2$ group, a 5-membered ring optionally containing 1 to 3 nitrogen atom(s), a 6-membered ring optionally containing 1 to 3 nitrogen atom(s), or a condensed heterocycle that contains a 5-membered ring and a 6-membered ring optionally containing 1 to 3 nitrogen atom(s).

2. The hydrogel-forming material according to claim 1, wherein the fatty acid salt is selected from the group consisting of butyrates, valerates, caproates, enanthates, caprylates, pelargonates, caprates, laurates, myristates, pentadecylates, palmitates, palmitoleates, margarates, stearates, oleates, vaccenates, linoleates, (9,12,15)-linolenates, (6,9,12)-linolenates, eleostearates, tuberculostearates, arachidates, arachidonates, behenates, lignocerates, nervonates, cerotates, montanates, and melissates.

3. The hydrogel-forming material according to claim 1, wherein the disperse phase (A) further includes a polyhydric alcohol.

4. The hydrogel-forming material according to claim 1, wherein the disperse phase (B) further includes a polyhydric alcohol.

5. A method for producing a hydrogel comprising:
   preparing the disperse phase (A) including a lipid peptide-based gelator, water, and a fatty acid salt as claimed in claim 1;
   adding the disperse phase (B) including a water-soluble acidic polymer as claimed in claim 1 to the disperse phase (A); and
   stirring the resulting mixture at room temperature and then leaving the resulting mixture still standing to form a hydrogel.

6. The method for producing a hydrogel according to claim 5, wherein preparation of the disperse phase (A) is performed by mixing the lipid peptide-based gelator, water, and the fatty acid salt at a high temperature with stirring and then leaving the resulting mixture to cool to reach room temperature.

7. A hydrogel formed from the hydrogel-forming material as claimed in claim 1.

8. A hydrogel formed from the hydrogel-forming material as claimed in claim 2.

9. A hydrogel formed from the hydrogel-forming material as claimed in claim 3.

10. A hydrogel formed from the hydrogel-forming material as claimed in claim 4.

* * * * *